(12) United States Patent
Titus et al.

(10) Patent No.: US 12,201,419 B2
(45) Date of Patent: Jan. 21, 2025

(54) INFRARED SPECTROSCOPIC DEVICES AND METHODS OF USE FOR TRANSDERMAL PATIENT ASSESSMENT

(71) Applicant: RCE Technologies, Inc., Bermuda Dunes, CA (US)

(72) Inventors: Jitto Titus, Acworth, GA (US); Atandra Burman, Bermuda Dunes, CA (US)

(73) Assignee: RCE Technologies, Inc, Carlsbad, CA (US)

( * ) Notice: Subject to any disclaimer, the term of this patent is extended or adjusted under 35 U.S.C. 154(b) by 403 days.

(21) Appl. No.: 17/537,932

(22) Filed: Nov. 30, 2021

(65) Prior Publication Data

US 2022/0079473 A1 Mar. 17, 2022

Related U.S. Application Data

(63) Continuation-in-part of application No. 17/333,118, filed on May 28, 2021.
(Continued)

(51) Int. Cl.
*A61B 5/1455* (2006.01)
*A61B 5/00* (2006.01)
(Continued)

(52) U.S. Cl.
CPC .......... *A61B 5/1455* (2013.01); *A61B 5/0075* (2013.01); *A61B 5/0261* (2013.01); *A61B 5/14546* (2013.01)

(58) Field of Classification Search
CPC ... A61B 5/1455; A61B 5/0075; A61B 5/0261; A61B 5/14546; A61B 5/742; A61B 5/6824; A61B 5/6831
See application file for complete search history.

(56) References Cited

U.S. PATENT DOCUMENTS 7,133,710 B2 * 11/2006 Acosta ................ A61B 5/1455
600/316
9,936,908 B1    4/2018 Acosta et al.
(Continued)

FOREIGN PATENT DOCUMENTS

DE    102016008885 A1    1/2018

OTHER PUBLICATIONS

Burman et al., "Cardiac Injury Risk Stratification Based On Non-Invasively Obtained Optical Sensor Device Data," U.S. Appl. No. 63/032,904, filed Jun. 1, 2020.
(Continued)

*Primary Examiner* — Sean D Mattson
(74) *Attorney, Agent, or Firm* — Quinn IP Law

(57) ABSTRACT

One or more aspects of the technical solutions described herein facilitate using transdermal infrared optics to discover infraspectral markers. The infraspectral markers can predict presence/absence of one or more physiological state in a subject. One or more aspects of the technical solutions described herein further facilitate continuous monitoring and prediction of trends of a physiological state of a subject using non-invasive transdermal infrared optics. Further, one or more aspects of the technical solutions described herein facilitate personalized triage of and alerts for a subject based on continuous monitoring of non-invasive transdermal optical infraspectral markers.

17 Claims, 12 Drawing Sheets

Related U.S. Application Data

(60) Provisional application No. 63/148,384, filed on Feb. 11, 2021, provisional application No. 63/032,904, filed on Jun. 1, 2020.

(51) Int. Cl.
*A61B 5/026* (2006.01)
*A61B 5/145* (2006.01)

(56) References Cited

U.S. PATENT DOCUMENTS

| | | | |
|---|---|---|---|
| 2012/0253149 A1* | 10/2012 | Steuer | A61B 5/4845 |
| | | | 600/310 |
| 2015/0112168 A1* | 4/2015 | Conrad | G01R 33/24 |
| | | | 600/309 |
| 2016/0081597 A1* | 3/2016 | Bhavaraju | A61B 5/746 |
| | | | 600/365 |
| 2016/0095519 A1 | 4/2016 | Yamashita et al. | |
| 2016/0095550 A1 | 4/2016 | Lin et al. | |
| 2016/0097716 A1* | 4/2016 | Gulati | A61B 5/1495 |
| | | | 250/340 |
| 2017/0071550 A1* | 3/2017 | Newberry | A61B 5/14546 |
| 2017/0127983 A1* | 5/2017 | Spegazzini | A61B 5/1495 |
| 2017/0215796 A1 | 8/2017 | Giebeler et al. | |
| 2017/0281065 A1* | 10/2017 | Newberry | A61B 5/1455 |
| 2019/0342637 A1* | 11/2019 | Halac | A61B 5/14503 |
| 2020/0118679 A1 | 4/2020 | Burman et al. | |

OTHER PUBLICATIONS

PCT International Search Report and Written Opinion; Mailed: Oct. 29, 2021; Application No. PCT/US21/034700; Filed: May 28, 2021; 10 pages.

Titus et al., "Infrared Spectroscopic Devices and Methods of Use for Transdermal Assessment of Elevated Cardiac Troponin-I," U.S. Appl. No. 63/148,384, filed Feb. 11, 2021.

Titus et al., "Infrared Spectroscopic Devices and Methods of Use for Transdermal Patient Assessment," U.S. Appl. No. 17/333,118, filed May 28, 2021.

Supplementary Partial European Search Report for European application No. EP21818907, dated May 14, 2024.

* cited by examiner

INFRARED SPECTROSCOPIC DEVICES AND METHODS OF USE FOR TRANSDERMAL PATIENT ASSESSMENT

CROSS-REFERENCE TO RELATED APPLICATIONS

This application claims priority to U.S. Non-Provisional application Ser. No. 17/333,118, filed May 28, 2021, which claims priority to U.S. Provisional Application No. 63/148,384, filed Feb. 11, 2021, and U.S. Provisional Application No. 63/032,904, filed Jun. 1, 2020, the contents of which are incorporated by reference herein in their entireties.

BACKGROUND

The subject matter disclosed herein generally relates to medical diagnostic devices and methods and, more particularly, to transdermal patient assessment and diagnostic devices and methods.

Over ten million symptomatic patients present with chest pain in emergency departments in the United States each year. Over 80% of these are due to non-cardiac causes, resulting in an unnecessary burden in the emergency departments. This reveals a need for non-invasive detection techniques that can streamline the emergency department workflows, preferably with a rapid testing mechanism for timely analysis. Furthermore, one out of five myocardial infarctions is asymptomatic (silent), leading to nearly 200,000 silent myocardial infarctions each year in the US. Therefore, the development of new technologies that can allow early non-invasive detection of myocardial injury is imperative.

State-of-the-art for troponin assays involve the use of two or more antibodies, one of which is labeled, typically with a chemiluminescent tag, which add another level of complexity in the analysis. While recent point-of-care (POC) solutions have reduced the time required to obtain test results, there still remains a dependency upon blood draws coupled with lower analytical sensitivity compared to central laboratory testing. This has resulted in limited application of such solutions toward effective discharge from emergency departments. Accordingly, improved solutions are desired to improve emergency room discharge and patient diagnostics and evaluation.

SUMMARY

According to some embodiments transdermal optical sensing systems are provided. The systems include a main body, an internal reflection element arranged within the main body, with an internal reflection element surface exposed for contact with an epidermis, an optical source configured to project light into the internal reflection element, an optical detector arranged to detect reflected light that reflects internally within the internal reflection element due to total internal reflection, a controller configured to measure the light at the optical detector to determine the presence of one or more compounds within the epidermis, and a retention member attached to the main body, the retention member configured to wrap about a wrist of a patient.

In addition to one or more of the features described herein, or as an alternative, further embodiments of the transdermal optical sensing systems may include a base configured to provide at least one of electrical charging and electrical power to internal electronics within the main body, wherein the base is configured to removably receive the main body.

In addition to one or more of the features described herein, or as an alternative, further embodiments of the transdermal optical sensing systems may include a power source arranged within the housing, the power source configured to supply power to at least one of the controller, the optical source, and the optical detector.

In addition to one or more of the features described herein, or as an alternative, further embodiments of the transdermal optical sensing systems may include an operational button arranged on the main body, the operational button configured to enable control of the controller.

In addition to one or more of the features described herein, or as an alternative, further embodiments of the transdermal optical sensing systems may include an indicator light arranged on the main body configured to indicate an operational status of the transdermal optical sensing system.

In addition to one or more of the features described herein, or as an alternative, further embodiments of the transdermal optical sensing systems may include that the optical source is configured to generate infrared light.

In addition to one or more of the features described herein, or as an alternative, further embodiments of the transdermal optical sensing systems may include that the optical detector is configured to detect light at a range of 6.4-6.9 micrometers and a range of 8-14 micrometers.

In addition to one or more of the features described herein, or as an alternative, further embodiments of the transdermal optical sensing systems may include a band arranged about the internal reflection element.

In addition to one or more of the features described herein, or as an alternative, further embodiments of the transdermal optical sensing systems may include that the band is formed of soft or pliable material.

In addition to one or more of the features described herein, or as an alternative, further embodiments of the transdermal optical sensing systems may include at least one filter applied to the optical detector to filter one or more predefined optical wavelength ranges.

In addition to one or more of the features described herein, or as an alternative, further embodiments of the transdermal optical sensing systems may include that the main body comprises a first main body portion and a second main body portion connected by at least one retention member.

In addition to one or more of the features described herein, or as an alternative, further embodiments of the transdermal optical sensing systems may include that the optical source is configured to generate light at a predetermined pulse rate and the optical detector is configured to detect at a predetermined polling rate.

In addition to one or more of the features described herein, or as an alternative, further embodiments of the transdermal optical sensing systems may include that the predetermined polling rate is an integer multiple of the predetermined pulse rate.

In addition to one or more of the features described herein, or as an alternative, further embodiments of the transdermal optical sensing systems may include that the optical detector is one of a pyroelectric detector, a bolometer, and a microbolometer.

In addition to one or more of the features described herein, or as an alternative, further embodiments of the transdermal optical sensing systems may include that the optical detector is one of a thermocouple and a thermopile.

According to some embodiments, methods of monitoring biomarkers in a subject are provided. The methods include placing testing area of a patient in contact with an internal reflection element of a transdermal optical sensing system, the transdermal optical sensing system including an optical source and an optical detector operably connected to the internal reflection element, pulsing light from the optical source into the internal reflection element, detecting reflected light at the optical detector, collecting biomarker data based on the reflected light, and displaying the biomarker data.

In addition to one or more of the features described herein, or as an alternative, further embodiments of the methods may include performing a field calibration prior to placing the testing area in contact with the internal reflection element.

In addition to one or more of the features described herein, or as an alternative, further embodiments of the methods may include that the optical source is pulsed at a predetermined pulse rate and the optical detector polls at a predetermined polling rate, wherein the predetermined polling rate is an integer multiple of the predetermined pulse rate.

In addition to one or more of the features described herein, or as an alternative, further embodiments of the methods may include securing the testing area of the patient in contact with the internal reflection element using a retention member.

In addition to one or more of the features described herein, or as an alternative, further embodiments of the methods may include that the collecting of the biomarker data is performed continuously over a predetermined amount of time.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF THE DRAWINGS

The subject matter is particularly pointed out and distinctly claimed at the conclusion of the specification. The foregoing and other features, and advantages of the present disclosure are apparent from the following detailed description taken in conjunction with the accompanying drawings in which:

DETAILED DESCRIPTION

Figures 1A, 1B:
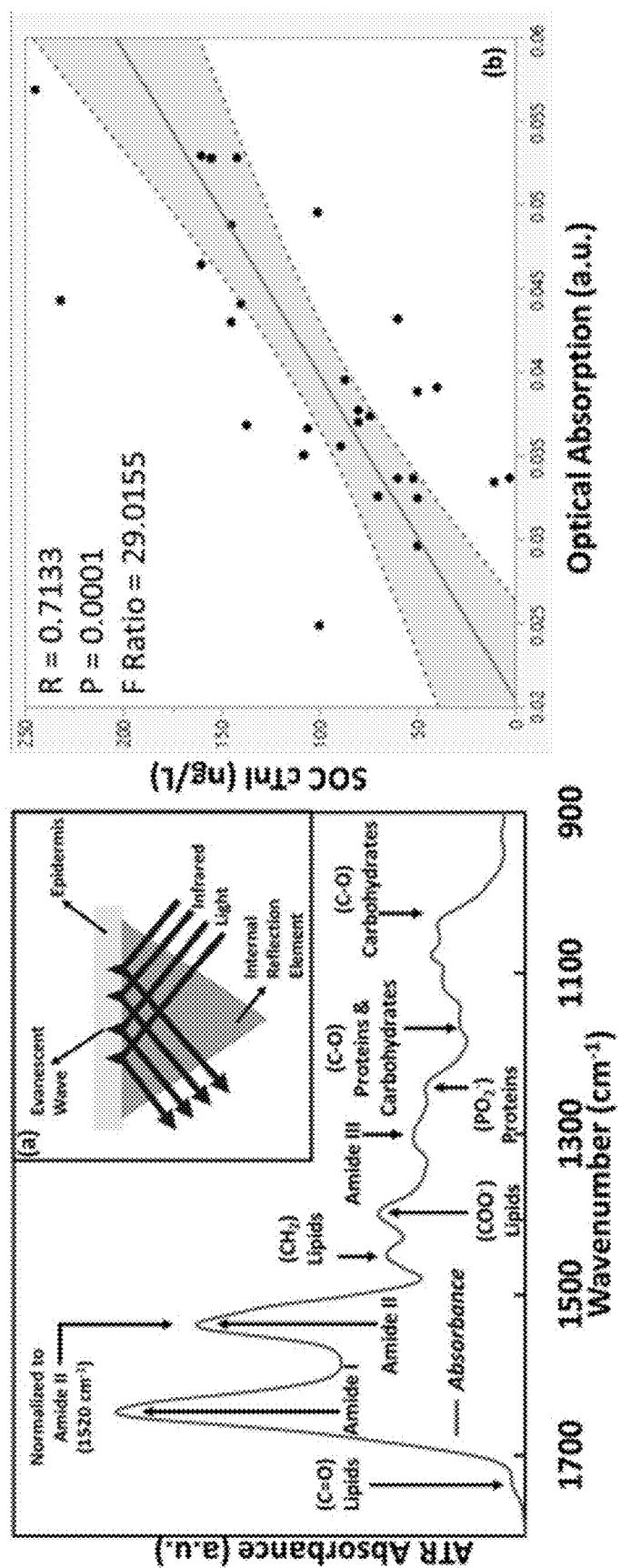
FIG. 1A is a schematic plot of characteristic peaks representative of individual molecular components, with the inset illustration of FIG. 1A illustrating a working principle of attenuated total reflectance in accordance with an embodiment of the present disclosure.
FIG. 1B illustrates a linear correlation between high sensitivity cTnI assay-derived data and the optical device absorption in accordance with an embodiment of the present disclosure.

Patient diagnostics may require complex testing and/or analysis. For example, the diagnosis of acute coronary syndrome (ACS), principally requires the monitoring of surface electrocardiograms and cardiac injury biomarkers within the clinical context. However, conventionally used biomarkers like cardiac troponins require invasive blood draws that can only be done periodically for the evaluation of ACS patients. Embodiments of the present disclosure are directed to transdermal monitoring of cardiac troponin-I (cTnI) to detect elevated states of the chemical. This may be achieved through use of non-invasive detection of cTnI-dependent infrared absorption. Using stepwise laboratory, benchtop, and clinical studies it has been determined there is a significant correlation between optically-derived data and blood-based immunoassay measurements. These data establish the potential of embodiments of the present disclosure for improving point-of-care risk stratification.

As noted above, many symptomatic patients present with chest pain in emergency departments in the United States each year, with over 80% of these due to non-cardiac causes. This results in an unnecessary burden upon emergency departments, hospitals, and other healthcare institutions. Embodiments of the present disclosure may provide for an instant, non-invasive detection technique that can streamline patient care in such symptomatic patients. Furthermore, as noted a significant percentage of myocardial infarctions are asymptomatic (e.g., silent). Embodiments of the present disclosure may provide for early non-invasive detection of myocardial injury.

State-of-the-art for troponin assays involve use of two or more antibodies, one of which is labeled, typically with a chemiluminescent tag. This tagging and process can add additional levels of complexity in analysis and diagnostic procedures. While recent point-of-care (POC) solutions may reduce time to test results, there still remains a dependency upon blood draw from a patient coupled with lower analytical sensitivity compared to central laboratory testing. As such, these in-field applications (e.g., at an emergency department) may be limited in their application toward effective patient discharge.

Embodiments of the present disclosure are directed to solutions employing infrared spectroscopy. Infrared spectroscopy provides a characterization technique from the ability to probe into a material at a molecular level. This molecular level probing can provide for an inherently sensitive mode of interrogation. Advantageously, by employing such techniques, minimal or no sample preparation may be required (and no blood draws or the like are required). That is, similar to pulse oximeters, breathalyzers, and bilirubinometers, a sample is not taken from the body of a patient in the non-invasive procedures described herein.

Infrared spectroscopy has some drawbacks which have limited the application in point of care and diagnostic processes with a patient, for example, in an emergency room. Firstly, signal-to-noise ratios strongly dictate the minimum detectable limit, and thus may bound the applicability for in situ applications (e.g., no clinic/lab controls). Secondly, because all matter is a source of infrared radiation, efficiencies of IR-based devices can be confounded by stray (e.g., ambient) light. Finally, the most sensitive mode of operation (which is Fourier Transform IR spectroscopy) requires a large footprint and is highly sensitive to mechanical vibrations, due to moving components. As such, the most sensitive application is often confined to ex vivo modalities (e.g., not directly at the patient). Embodiments of the present disclosure may provide for solutions that may mitigate or entirely eliminate the above mentioned challenges, in addition to providing other advantages and improvements in the field of patient diagnostics. In view of this, embodiments of the present disclosure are directed to an efficacious, non-invasive device capable of risk-stratifying patients based on IR detected chemicals. In some non-limiting embodiments, the devices disclosed herein may enable efficacious, non-invasive devices capable of risk-stratifying ACS patients based on Troponin-I levels.

Absorption spectroscopy is a molecular characterization technique typically used to study the composition of materials and thereby determine concentrations of the substance of interest in a native state. When infrared radiation is incident on a material such that the energy is equivalent to the chemical bond vibrational mode of the material, there is energy transfer causing the absorption of the light radiation leading to an active vibrational mode. This results in certain energies or wavelengths of light being absorbed by the material that are unique to the material. Thus, the material can be compositionally characterized by performing a differential measurement of the light before and after it passes through the material.

Traditional configurations of absorption spectroscopy involve directing infrared radiation through a sample to be measured and detecting the light on the opposite side using a thermal or optical detector. This restricts the mode of interrogation to in vitro or ex vivo measurement. To overcome this issue, embodiments of the present disclosure are directed to employing an Attenuated Total Reflectance (ATR) configuration. In ATR configurations of the present disclosure, light is totally internally reflected inside an internal reflection element or prism of a higher refractive index than the material to be characterized (e.g., blood). Photons come out of the surface of the crystal penetrating the sample (e.g., skin) and then are coupled back into the system. This partially penetrated evanescent wave can interact with the material on the surface of the crystal, affording the intensities of the frequencies of light measured after passing through the prism to be highly sensitive to the materials present on the surface of the crystal. The penetration depth of the photons is a function of the wavelength of light and the refractive indices of the internal reflection element crystal and sample. In the optical sensor/detector design of embodiments of the present disclosure, mid-infrared radiation is introduced into an internal reflection element. Such internal reflection elements, in accordance with embodiments of the disclosure and as example only, may be germanium, zinc sulfide crystals. After the infrared light totally internally reflects at a contact surface of the internal reflection element, the infrared light may be detected by an infrared detector. In accordance with some embodiments, the signals before and after the internal reflection element makes contact with the sample are differentially processed to obtain optical characteristics of the sample.

Referring now to FIGS. 1A-1B, schematic plots of various vibrational modes observed when mid-infrared light (MIR) interacts with the epidermis of a patient in an Attenuated Total Reflectance (ATR) configuration are shown. FIG. 1A indicates the characteristic peaks representative of individual molecular components, the inset illustration of FIG. 1A illustrates the working principle of Attenuated Total Reflectance. FIG. 1B illustrates a linear correlation of 71% was observed between the high sensitivity cTnI assay-derived data and the optical device absorption (n=30).

In the plot of FIG. 1A, the vertical axis is an absorbance (ATR) in absorbance units (a.u.) and the horizontal axis is wavenumber in reciprocal centimeter ($cm^{-1}$). In the plot of FIG. 1B, the vertical axis is cTnI (high sensitivity cardiac troponin-I assay (hs-cTnI)) in nanogram per liter (ng/L) and the horizontal axis is optical absorption in absorbance units (a.u.), R refers to the linear coefficient of correlation and P is the p-value associated with the correlation, and a higher F-ratio indicates the degree of deviation from the null hypothesis.

As shown in FIG. 1A, peaks representative of specific chemical compositions may be obtained through a device configured to perform Attenuated Total Reflectance upon a surface (e.g., epidermis of a patient). As shown in the insert of FIG. 1A, infrared light is passed into and through an internal reflection element that is arranged in contact with the epidermis. The infrared light will internally reflect within the interior reflection element and the reflected infrared light may be monitored to obtain the peak data illustrated in FIG. 1A. As shown, an evanescent wave may penetrate into the epidermis.

An investigational study was conducted to determine the spectral features that are unique to cardiac markers such as cardiac Troponin I, creatine kinase-MB, and B-type natriuretic peptide (BNP), with the optical characterization of these substances in their pure form. This measurement was carried out using an infrared spectrometer employing a diamond IRE, to identify a unique concert of absorption features that can be deemed as a signature for cardiac troponin. This allows one to optically detect and quantify the presence of that particular biomarker in a host substrate such as whole blood. De-identified healthy whole blood was procured and characterized to determine if there are any confounding overlaps in the absorption peaks of blood and cardiac biomarkers. Consequently, to confirm the efficacy of ATR mode of interrogation, a number of de-identified blood samples with the corresponding measurement of high sensitivity cardiac troponin values were procured. Patients were identified with a spectrum of Troponin-I values between the limits of detection of the assay namely, a cardiac troponin-I assay (e.g., hs-cTnI). The blood samples were then optically characterized ex vivo with the modality of total internal reflection using a research-grade benchtop Fourier Transform infrared spectrometer employing a diamond IRE. Each blood sample to be characterized was one microliter in volume as deposited on the IRE. Each sample was measured in triplicate, with every repeat being an average of 32 co-added scans at a resolution of 4 $cm^{-1}$. The optical readouts were investigated for correlation (as illustrated in FIG. 1B) with that of cTnI concentrations. A positive linear correlation of 71% (p=0.0001) was observed between optical and troponin-I data within the range of 2.5 to 250 ng/L.

Embodiments of the present disclosure are directed to ambulatory, non-invasive trans-dermal wearable devices. The wearable devices may be installed on the wrist of a patient or arranged in contact with the skin of a patient (e.g., at locations other than the wrist).

Figure 2A:
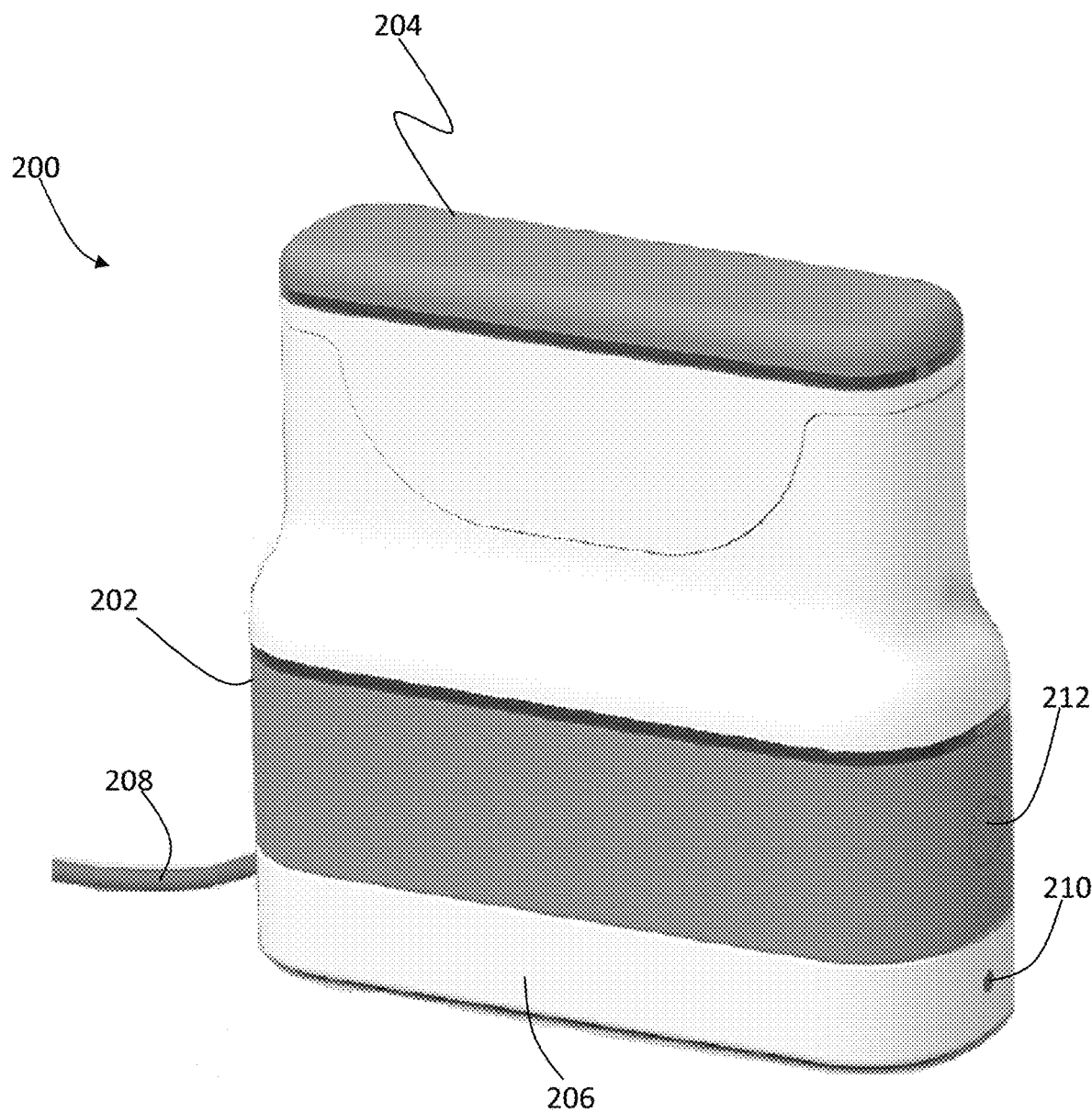
FIG. 2A is a schematic illustration of a transdermal optical sensing system in accordance with an embodiment of the present disclosure.
Figure 2B:
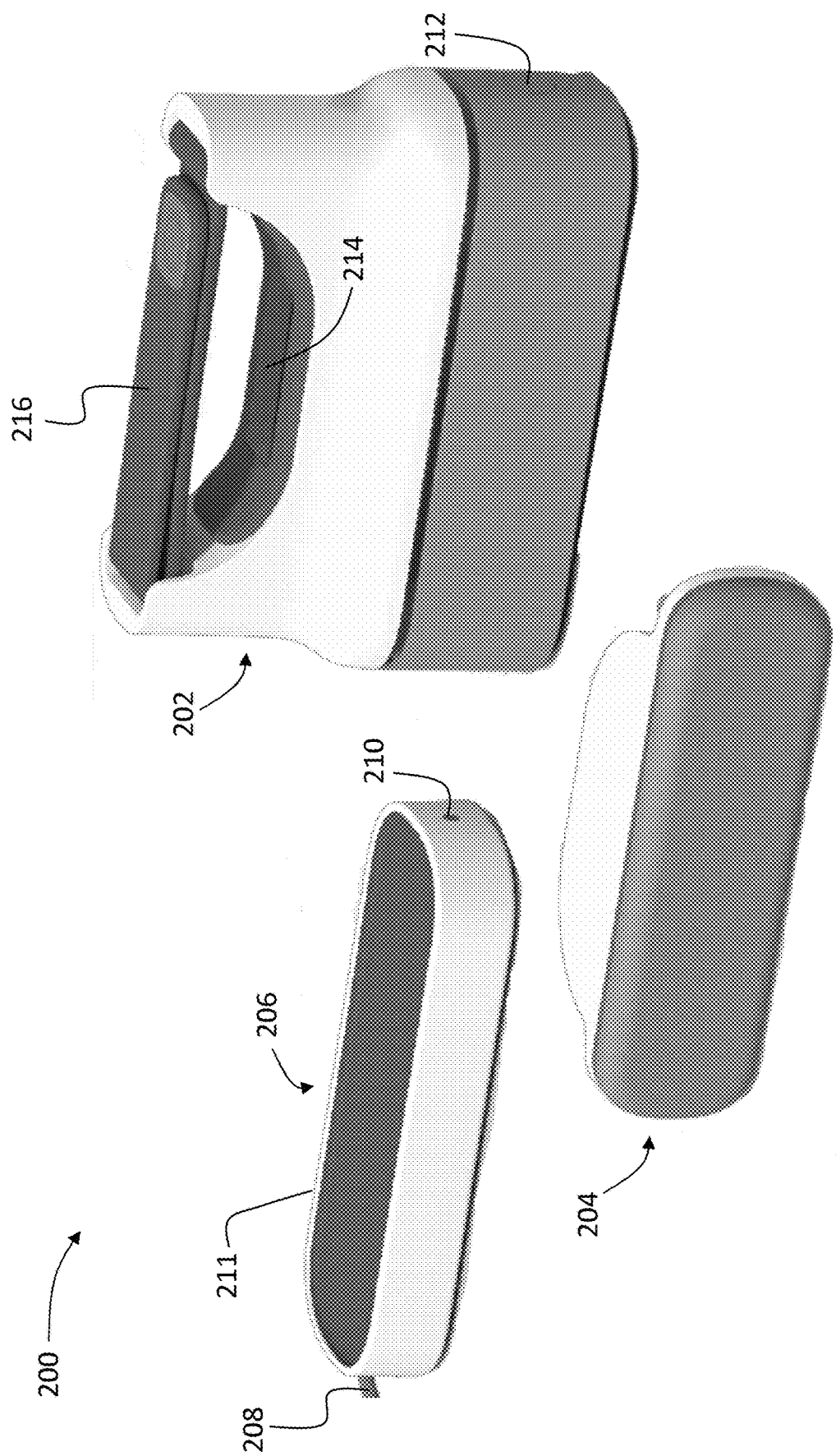
FIG. 2B illustrates components of the transdermal optical sensing system of FIG. 2A as separated from each other.

Referring now to FIGS. 2A-2B, schematic illustrations of a transdermal optical sensing system 200 in accordance with an embodiment of the present disclosure are shown. FIG. 2A illustrates the transdermal optical sensing system 200 as assembled and FIG. 2B illustrates the transdermal optical sensing system 200 with the components thereof separated. The transdermal optical sensing system 200 includes a main body 202, cover 204, and a base 206. The main body 202 may be configured as a housing or enclosing structure configured to house electrical and optical components therein, as described below. The cover 204 is configured to removably cover a portion of the main body 202 and may be attachable to the main body 202 by snap engagement, sliding fit, or otherwise, as will be appreciated by those of skill in the art. The cover 204 may be configured to provide a sealing cover of components of the main body 202.

The base 206, in this embodiment, is configured to enable charging of electrical components of the main body 202. As shown, the base 206 includes a power cable 208 that may be plugged into a power source, such as a wall outlet, a charged-USB port, a battery, or the like. In some embodiments, the base 206 may be configured to provide wireless charging to electrical components within the main body 202. In other embodiments, an electrical port connection (e.g., USB, pin-connection, etc.) may be provided to enable physical electrical connection between the base 206 and the main body 202. In this configuration, the base 206 also includes an optional indicator light 210. The indicator light 210 may be provided to indicate a charging state or other operational state of the electronics of the main body 202 and/or of the transdermal optical sensing system 200. The base 206 may also have a lip 211 or other structural feature (e.g., protrusion, rim, etc.) that is configured to enable proper positioning and alignment of the main body 202 on the base 206, such as for the purpose of charging and/or data transmission. In some embodiments, rather than the lip 211 around a periphery of the base 206, or in combination therewith, a central feature, such as a protrusion or depression may be used that mates with a companion feature (e.g., depression or protrusion) of the main body 202.

The main body 202, in this illustrative embodiment, includes an operational button 212. The operational button 212 may be configured to enable powering the electronics of the main body 202 on and off. Further, in some embodiments, the operational button 212 may be configured to enable use of the transdermal optical sensing system 200 (e.g., to perform a diagnostic operation as described herein). In some embodiments that have a single operational button 212, the single operational button 212 may be configured to have different actuation mechanisms to achieve different operational states. For example, a long press may be configured for powering on or off the transdermal optical sensing system 200. A single press or a multi-press may enable operation of the transdermal optical sensing system 200 to perform a diagnostic operation. In other embodiments, multiple operational buttons may be configured on main body 202 for performing different functions. Further still, in some embodiments, the operational button 212 may be omitted, and the transdermal optical sensing system 200 may be configured to be controlled or operated by a remote device (e.g., remote controller, mobile device, computer, smart phone, etc.). It will be appreciated that various different control and/or power button options are possible without departing from the scope of the present disclosure.

FIG. 2B illustrates the transdermal optical sensing system 200 with the base 206 and the cover 204 separated from the main body 202. As shown, the main body 202 includes an internal reflection element 214 (also referred to as IRE 214) and a retention member 216. The IRE 214 may be an internal reflection element, such as a prism, crystal, or the like, as described above. The IRE 214 is positioned and arranged within the main body 202 such that a portion of the IRE 214 is exposed. The IRE 214 may be optically coupled to an optical source and an optical detector (e.g., both IR wavelength source/detector) that are arranged within the main body 202. The exposed portion of the IRE 214 is arranged such that the wrist or other part of a patient's body may be arranged in contact with the IRE 214. The main body 202 may be shaped and contoured to aid in ensuring that appropriate contact between the epidermis of a patient remains in contact with the IRE 214 when performing a diagnostic operation. The retention member 216 is an optional element and can be provided to further aid in ensuring contact between epidermis and the IRE 214.

The retention member 216 may be a strap, band or other structure that can partially wrap about a patient's wrist and retain the wrist in a position of constant contact with the IRE 214. The retention member 216 can include securing means, such as a buckle, pin-and-hole connection, hook-and-loop connection, snap-buttons, magnetic clasp, a tie strap, or the like, as will be appreciated by those of skill in the art. In some embodiments, a strap or other band may be housed or retained within the main body 202, and may be wound or tensions (e.g., like a seatbelt) and may be configured for auto-tensioning once a wrist is placed on the transdermal optical sensing system 200.

The transdermal optical sensing system 200 may be a portable or semi-portable device. In some embodiments, the transdermal optical sensing system 200 may be a desktop or tabletop device, that can be moved around from place to place. In some embodiments, the transdermal optical sensing system 200 may be configured and sized for bedside use, and thus has a relatively small form factor that can fit on a hospital bed, or the like, with a patient and not disrupt such patient.

Figure 3:
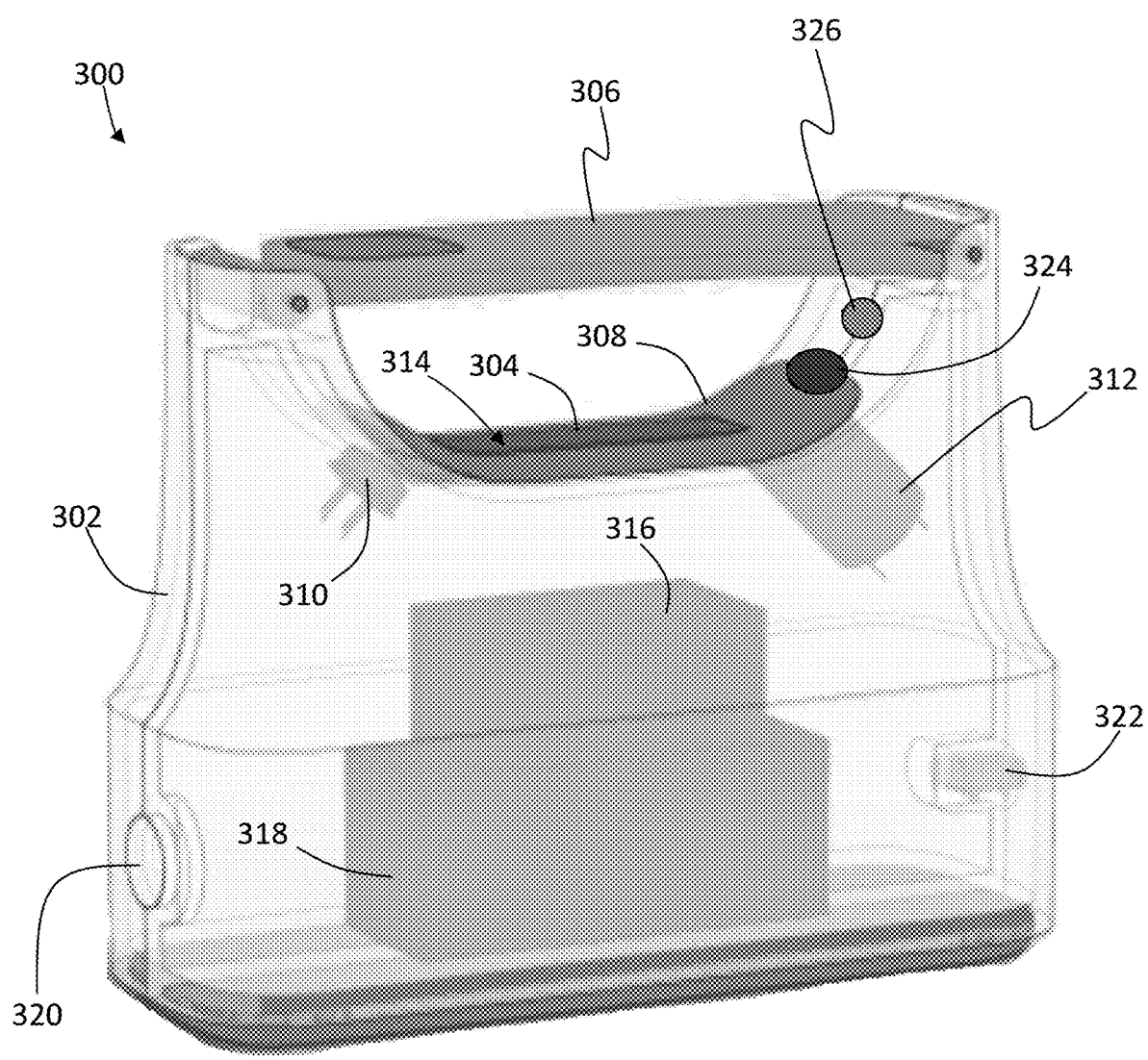
FIG. 3 is a schematic illustration of a transdermal optical sensing system in accordance with the present disclosure.

Turning now to FIG. 3, a schematic illustration of a transdermal optical sensing system 300 in accordance with an embodiment of the present disclosure is shown. The transdermal optical sensing system 300 is similar to that in configuration as the transdermal optical sensing system 200 of FIGS. 2A-2B. In the illustration of FIG. 3, the transdermal optical sensing system 300 is not shown with a cover or base, as described above, but can be configured to include such elements.

The transdermal optical sensing system 300 includes a main body 302 that houses internal electronics and defines a slot or area for a patient to put their epidermis in contact with an IRE. As shown, the transdermal optical sensing system 300 includes an IRE 304 and a retention member 306 for holding a patient's wrist in contact with the IRE 304. The IRE 304 may be surrounded by a band 308. The band 308 may be a soft or pliable material to aid in comfort to a patient. Further, the material of the band 308 may be selected to compress when a wrist is resting thereon, and thus the epidermis of the patient may contact the IRE 304. For example, the band may be formed of rubber or the like. The band 308 may prevent debris or particulates from entering into the main body 302.

The IRE 304 is optically coupled to an optical source 310 and an optical receiver 312. The optical source 310 is an electronic element that is configured to generate one or more wavelengths of light to be projected into the IRE 304. In some embodiments, the wavelength(s) of light generated by the optical source 310 may be within the infrared optical band. The optical source 310 may be a 2-channel optical source, a 4-channel optical source, a multichannel optical source, or the like. It will be appreciated that any number of channels, including a single channel, may be used, without departing from the scope of the present disclosure. The incident light is directed to an IRE surface 314 of the IRE 304. When a patient has placed their epidermis in contact with the IRE 304, the incident light will contact and interact with the epidermis at the IRE surface 314. After interaction with the epidermis at the IRE surface 314, the light will internally reflect within the IRE 304 and the reflected light may be detected by the optical receiver 312. The optical receiver 312 may be configured to detect the wavelength, amplitude, or other characteristics of the reflected light.

The transdermal optical sensing system 300 includes internal electronics including, at least, a controller 316 and a power source 318. The power source 318 is configured to supply electrical power to, at least, the controller 316, the optical source 310, and the optical receiver 312. The controller 316 may be operably coupled to each of the optical source 310 and the optical receiver 312. Such operably coupling may be by electrical wires or by wireless connection. The controller 316 may be configured to cause light generation at the optical source 310. Further, the controller 316 may be configured to receive data or information from the optical receiver 312 in order to perform analysis thereon. In some embodiments, the controller 316 may be configured to transmit data received from the optical receiver 316 to an external component, such as a smart phone, a mobile device, a computer, a cloud network, etc. In some such embodiments, processing and analysis of the information or data detected at the optical receiver 312 may be processed for diagnostic purposes at the remote component. In other embodiments, the processing may be performed at the controller 316. The transdermal optical sensing system 300 also includes an operational button 320 and an indicator light 322 that may be configured similar to that described above.

The controller 316 is configured to process the electrical data extracted from the detector (optical receiver 312) and emitter (optical source 310). The processing involves a differential between the "on" and "off" state of the optical source 310 to remove the effects of ambient conditions. Further, in accordance with some embodiments, four channels of data extracted from the optical receiver 312 may be differentially processed with one channel always being used as a reference, allowing for standardization. For example, in some such embodiments, a first channel may be used for calibration, normalization, and/or reference of the other three channels. In other embodiments, a two channel system may be used, or a multichannel system, where a scan is performed through a range continuously or incrementally. Further, in some embodiments, a single channel configuration may be employed. Patient data may also be weighted by the background data in order to obtain absolute values. Finally, the controller 316 is configured to output a troponin value on a display (e.g., on the optical sensing system and/or on a remote display or portal).

In some embodiments, the transdermal optical sensing system 300 can include additional sensors or detectors. For example, an EKG sensor 324 may be provided on or near the band 308 and positioned such that when a user or patient places their wrist on the transdermal optical sensing system 300, the wrist will contact the IRE surface 314 of the IRE 304 and the EKG sensor 324. The EKG sensor 324 may include one or more contact points (e.g., two) for ensuring detection of heart rate during a measurement taken by the transdermal optical sensing system 300. As such, biomarker data and heart rate data may be obtained and collected simultaneously. Advantageously, such data collection can enable improved health monitoring by correlating various types of data of the patient. The EKG sensor 324 may be an electrical component that is electrically connected to and controller by the controller 316. The transdermal optical sensing system 300 may also include one or more detection sensors 326. The detection sensor 326 may be an optical or other type of proximity sensor and/or may be a pressure sensor. The detection sensor 326 may be connected to the controller 316 and can enable proper detection and measurements. For example, the controller 316 may be configured to perform a measurement operation only when the detection sensor 326 detects the presence of a wrist (or other body part) positioned on the transdermal optical sensing system 300.

Figure 4A:
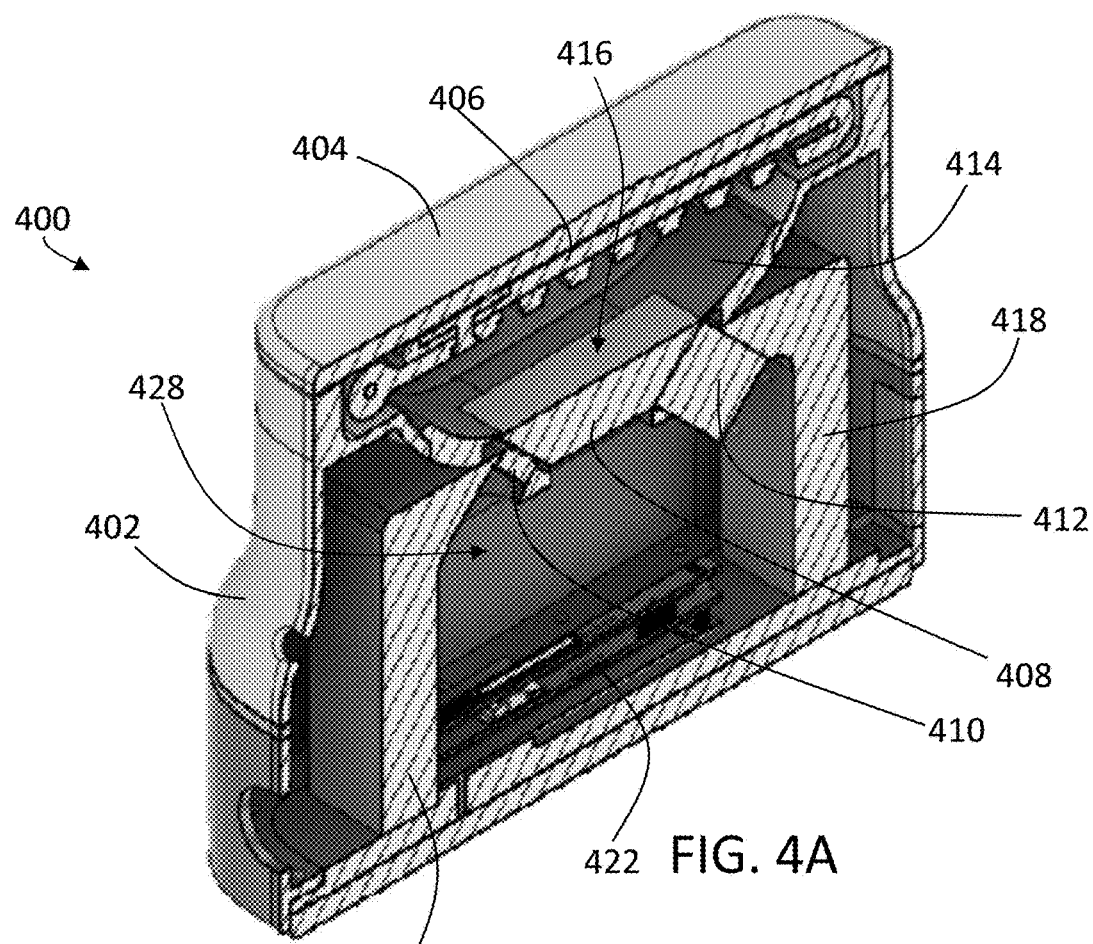
FIG. 4A is a cross-sectional illustration of a transdermal optical sensing system in accordance with an embodiment of the present disclosure.
Figure 4B:
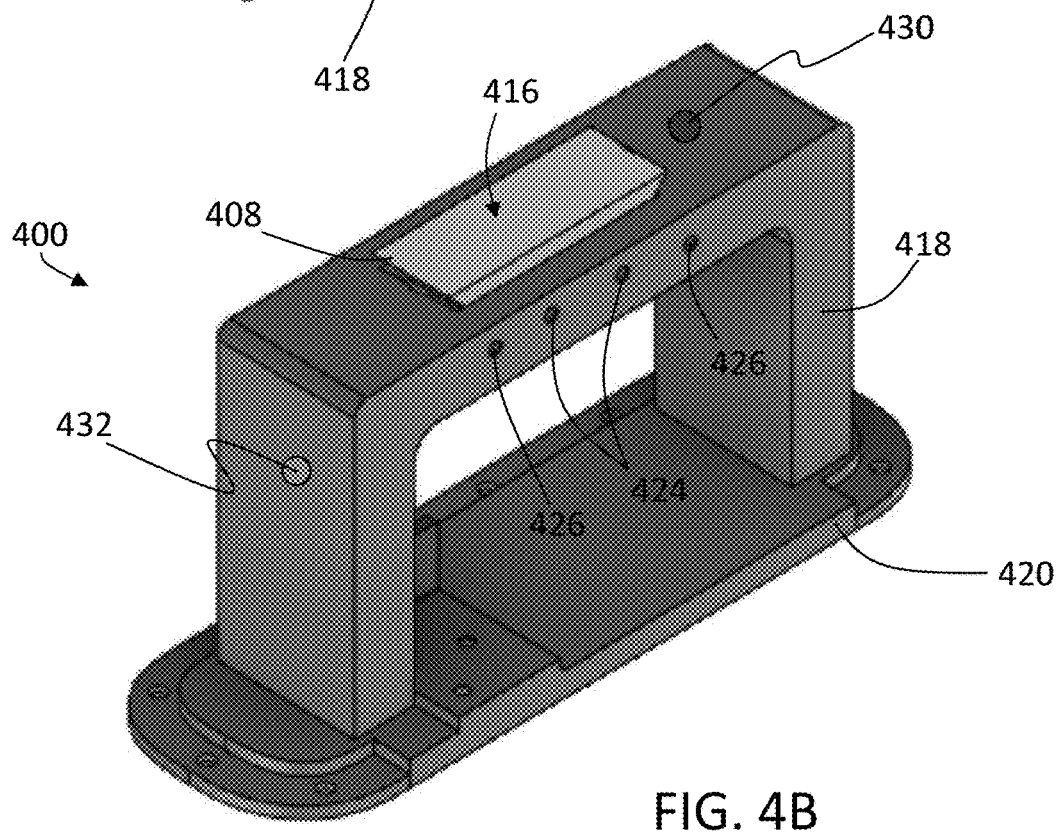
FIG. 4B is a schematic illustration of components of the transdermal optical sensing system of FIG. 4A.

Turning now to FIGS. 4A-4B, schematic illustrations of a transdermal optical sensing system 400 in accordance with an embodiment of the present disclosure are shown. FIG. 4A illustrates a cross-sectional view of the transdermal optical sensing system 400 and FIG. 4B illustrates a structural arrangement of components of the transdermal optical sensing system 400. The transdermal optical sensing system 400 may be similar to that shown and described above.

The transdermal optical sensing system 400 includes a main body 402 with a cover 404 removably attached thereto. A retention member 406 is attached to the main body 402, similar to that described above. The transdermal optical sensing system 400 includes an IRE 408 with associated optical source 410 and optical detector 412. A band 414 is arranged about an IRE surface 416, similar to that described above.

Within the main body 402 of the transdermal optical sensing system 400, a structural frame 418 is provided to support the IRE 408 and components associated therewith. The structural frame 418 may extend upward from a structural base 420 which is configured to be affixed within the main body 402 and support the structural frame 418. The structural frame 418 may be configured to dissipate force away from electrical components 422 of the transdermal optical sensing system 400. Further, the structural frame 418 may enable isolating of the optical elements from mechanical vibrations and/or provide for heat dissipation through the material selection of the structural frame 418. The structural base 420 may be configured to house and/or support the electronic components 422 and/or power components (not shown for clarity). The electronic components 422 can include processors, input/output elements, power control circuits, and/or other printed circuit boards or the like, as will be appreciated by those of skill in the art. The power components can include batteries and/or hardwired electrical power components (e.g., wireless charging elements, ports, power cable, etc.).

In accordance with some embodiments of the present disclosure, and as shown in FIG. 4B, the IRE 408 may be mounted or affixed within and/or to the structural frame 418 by one or more mounting screws or set screws 424. Similarly, the optical source 410 and the optical detector 412 may be mounted or affixed within and/or to the structural frame 418 by one or more mounting or set screws 426. The set screws 424, 426 are configured to position and hold the optical elements (e.g., IRE 408, optical source 410, optical detector 412) at required angles relative to each other within the structural frame 418.

In some embodiments, the set screws 424, 426 may be soft-tipped screws that can help with vibration isolation of the components supported (e.g., the IRE 408, the optical source 410, the optical detector 412). The soft-tipped set screws may be tipped with a polymer, plastic, or rubber materials, and may be nylon or the like. If the screws are not fully made from soft or pliable materials, and only tipped with such material, the screws may be made from metal or the like, including, but not limited to steel, stainless steel, brass, etc. The vibration isolation of the components (e.g., the IRE 408, the optical source 410, the optical detector 412) may further be aided by the material that forms the structural frame 418. For example, and without limitation, the structural frame 418 may be made from plastics, thermoplastics, polyethylene, high density polyethylene, polymers, and similar materials. Further, the material of the screws (or tips thereof) may be selected to avoid confounding of data collection (e.g., selected to avoid optical interference).

It will be appreciated that the electronic components (e.g., the optical source 410, the optical detector 412, and electronic components 422) may generate heat. To aid in heat dissipation, the main body 402 may have an open cavity 428 to provide air cooling to the components and remove heat therefrom. One or more vents (not shown) may be arranged about the exterior of the main body 402, to allow airflow through the interior open cavity 428. Further, in some embodiments, a fan or other blower may be arranged within the main body 402 to cause airflow within the open cavity 428. In some such embodiments, vents or the like may be included.

Furthermore, as noted above, the transdermal optical sensing systems of the present disclosure may include mechanisms for detecting the presence of a patient or user of the system. In some embodiments, as described above, such sensors may be arranged on the exterior of the main body. However, as shown in FIG. 4B, one or more detection sensors 430 may be arranged on the structural frame 418. In this configuration, the detection sensors 430 may be pressure sensors, for example. As such, when a user or patient places their wrist on the transdermal optical sensing system 400, the pressure and force of their wrist will be imparted to the structural frame 418, through at least contact with the IRE surface 416. As such, the detection sensors 430 may be configured to detect the presence of a user or patient when performing a measurement. The transdermal optical sensing systems may include other sensors, such as an accelerometer 432, shown in FIG. 4B. The accelerometer 432 may be used for detecting when a patient has placed their wrist in contact with the transdermal optical sensing system. The accelerometer 432 may also be used to monitor vibrations and motions of the transdermal optical sensing system 400. For example, the accelerometer 432 may be configured to monitor for falls or drops of the transdermal optical sensing system 400. If the transdermal optical sensing system 400 falls or is dropped, such impact may cause a change in the calibration and settings, and thus may indicate that the results of a testing or measurement may be incorrect. As such, the accelerometer 432 may be used to detect and/or indicate when recalibration and/or resetting of the system may be required.

Figure 5:
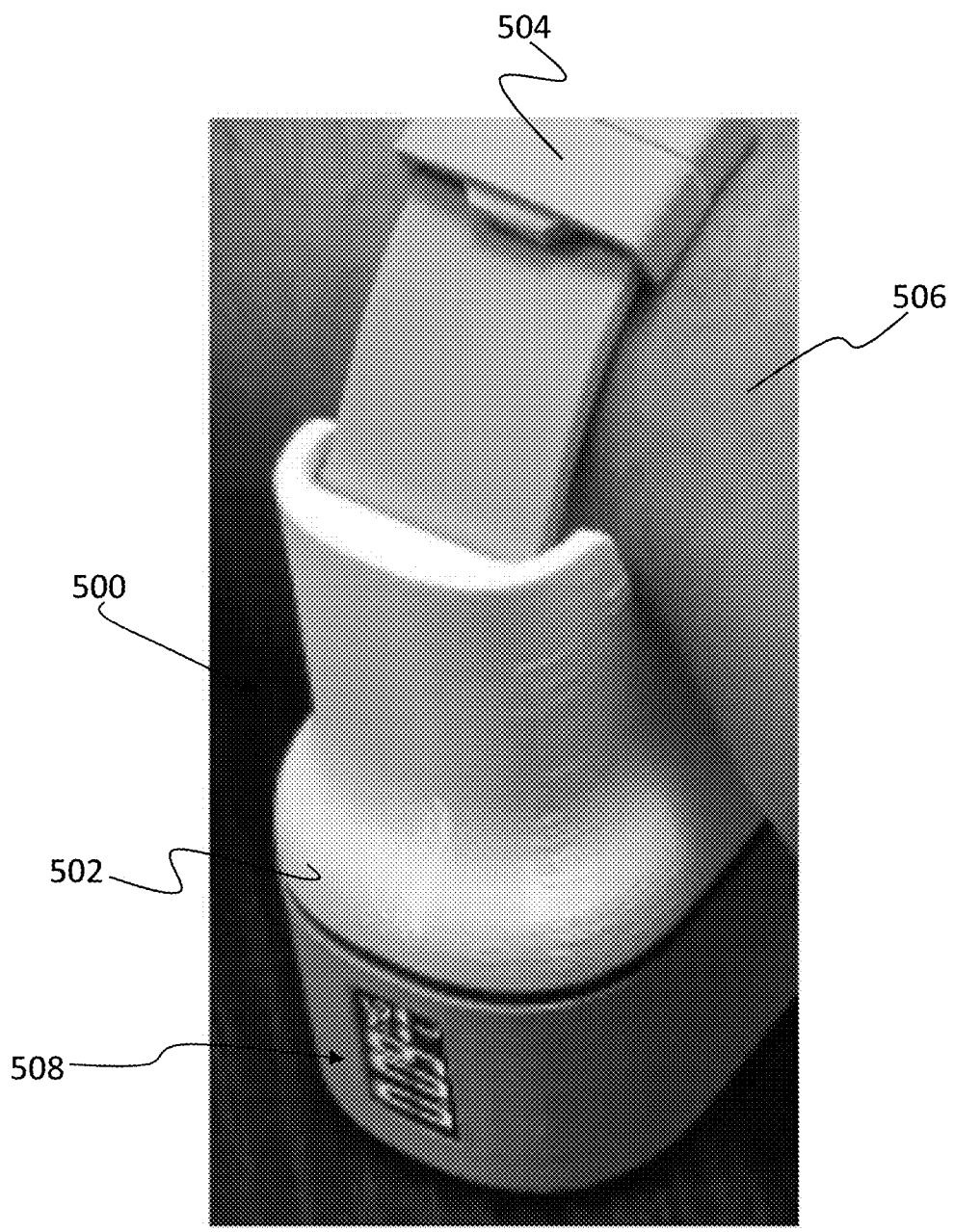
FIG. 5 is a schematic illustration of a transdermal optical sensing system in accordance with the present disclosure, when in use.

Turning now to FIG. 5, a schematic illustration of a transdermal optical sensing system 500 in use and in accordance with an embodiment of the present disclosure is shown. The structural configuration of the transdermal optical sensing system 500 may be substantially similar to that shown and described above. The transdermal optical sensing system 500 includes a main body 502 and a retention member 504. As shown, a patient 506 has their wrist secured to the transdermal optical sensing system 500 by the retention member 504. The retention member 504 provides support to hold the patient 506 in contact with an IRE of the transdermal optical sensing system 500.

In this configuration, the transdermal optical sensing system 500 includes a display 508 on a portion of the main body 502. The display 508 may be controlled by a controller or other electronic component of the transdermal optical sensing system 500. The display 508 may be used to output pertinent information for diagnostic purposes, such as detected levels of a biomarker, chemical, or compound of interest. It will be appreciated that the displayed information may be provided overtime, and thus enables trending of biomarkers in a patient. The display 508 may be used to provide instantaneous or real-time biomarker data/information and may be configured to display such measurements on a continuous basis. The display 508 may thus provide trending information in addition to, or alternative to, a current biomarker measurement. In some embodiments, the display may be separated from the transdermal optical sensing system, and may be part of a personal mobile device, computer, or the like.

Figure 6:
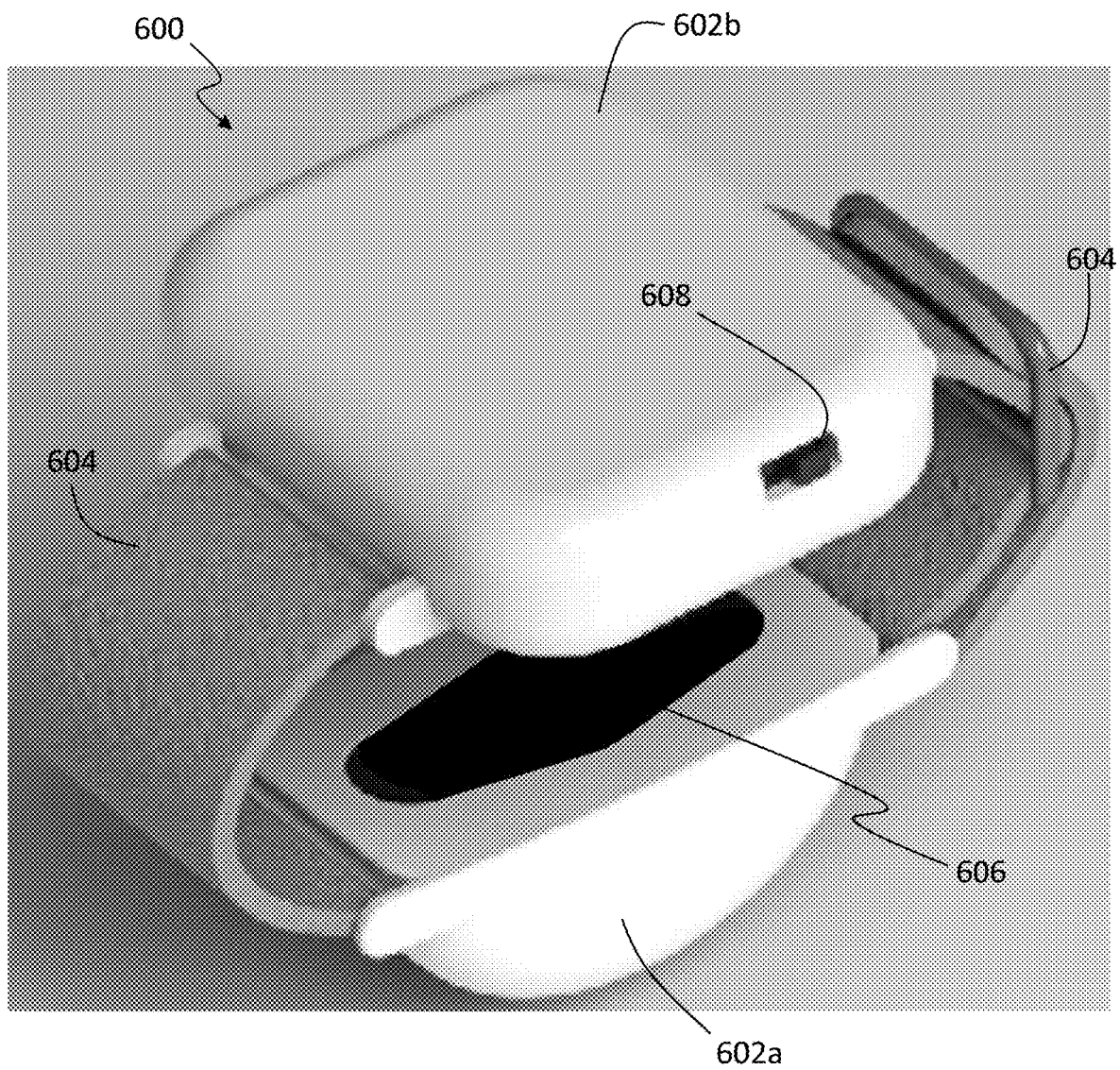
FIG. 6 is a schematic illustration of a transdermal optical sensing system in accordance with an embodiment of the present disclosure.

Although the above described and illustrated embodiments are fairly portable and mobile, in accordance with some embodiments of the disclosure, a more personal version of a transdermal optical sensing system may be provided. For example, with reference to FIG. 6, a schematic illustration of a transdermal optical sensing system 600 in accordance with an embodiment of the present disclosure is shown. The transdermal optical sensing system 600 operates substantially similar to that described above.

The transdermal optical sensing system 600, in this configuration, includes two main body portions 602a, 602b that are configured to house power and control features of the transdermal optical sensing system 600 (e.g., controller, electrical power, etc.). A first main body portion 602a may house the optical components and a second main body portion 602b may house the processing and control components of the transdermal optical sensing system 600. In this configuration, the transdermal optical sensing system 600 is arranged as a watch-type device or wrist-wearable and may be worn by a patient. As such, the transdermal optical sensing system 600 includes two retention members 604 that form a wristband or similar structure. The transdermal optical sensing system 600 includes an IRE 606 on the first main body portion 602a for contact with the skin of a patient that wears the transdermal optical sensing system 600. An operational button 608 may be provided to perform measurements on demand and/or for powering the transdermal optical sensing system 600 on and off.

Figure 7:
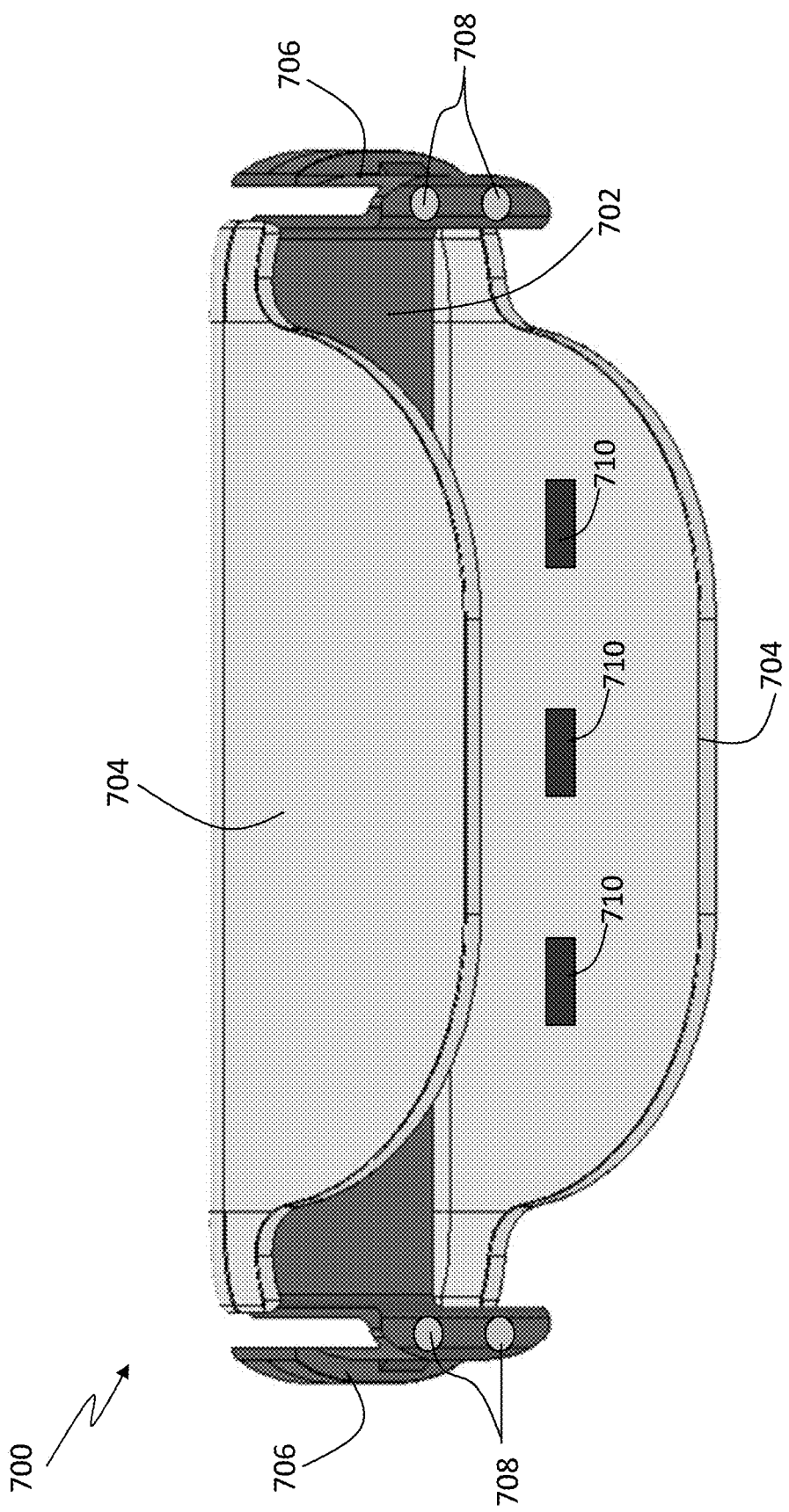
FIG. 7 is a schematic illustration of a cover of a transdermal optical sensing system in accordance with an embodiment of the present disclosure.

Turning now to FIG. 7, a schematic illustration of a cover 700 of a transdermal optical sensing system in accordance with an embodiment of the present disclosure is shown. The cover 700 may be used with any of the above described transdermal optical sensing systems or variations thereon.

The cover 700 is shown structurally to fit on the above described transdermal optical sensing systems, but such geometry and shape is not to be limiting and the cover may take other shapes, depending, for example, upon the geometry of the main body of the transdermal optical sensing system.

The cover 700 includes a top wall 702 and two sidewalls 704. As shown, the cover 700 includes clips 706 configured to snap-engage with a main body of a respective transdermal optical sensing system. It will be appreciated that other types of connections between the cover 700 and the main body may be employed without departing from the scope of the present disclosure. For example, in some non-limiting examples, a magnetic connection, the use of hooks, or the like may be used.

The cover 700, in this embodiment, includes electrical contacts 708 for transmission of electrical power from the main body into the cover 700. The cover 700 further includes one or more UV light emitters 710. The UV light emitters 710 may be powered through electrical power provided through the electrical contacts 708. The UV light emitters 710 may be arranged and angled such that light generated at the UV light emitters 710 are directed at an IRE of the transdermal optical sensing system to which the cover 700 may be attached. Such configuration enables disinfecting of the IRE through application of UV light incident thereto. Although shown with the UV light emitters 710 arranged on one sidewall 704 of the cover 700, it will be appreciated that such UV light emitters 710 may be included on both sidewalls 704 of the cover 700. Further, any number of UV light emitters 710 may be employed. Moreover, although described as UV light emitters, the cover 700 can include one or more types of emitters to generate light that may be used to disinfect or otherwise sanitize the IRE and other surfaces of the transdermal optical sensing system.

Figure 8:
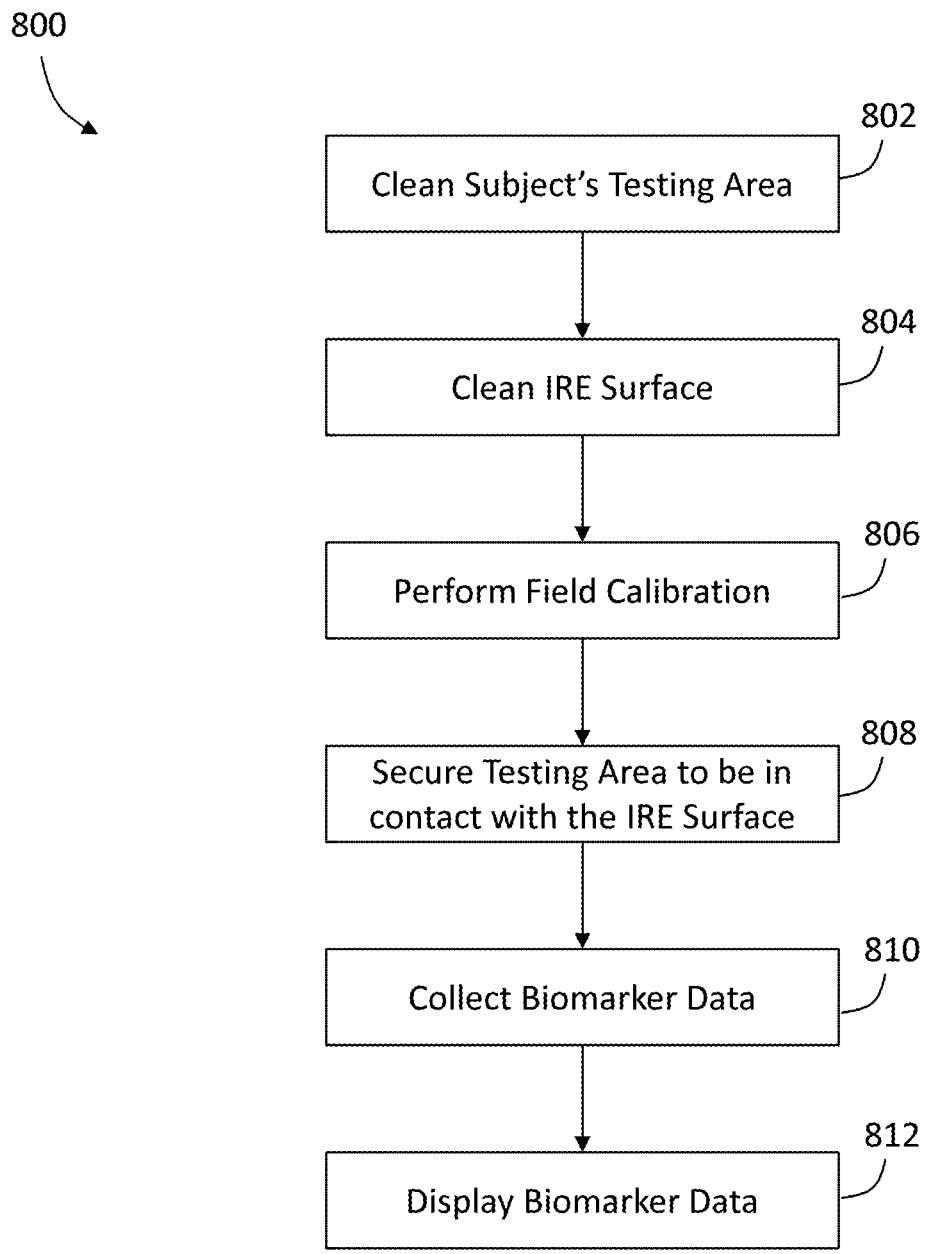
FIG. 8 is a flow process for using a transdermal optical sensing system in accordance with an embodiment of the present disclosure.

Turning now to FIG. 8, a flow process 800 for using a transdermal optical sensing system in accordance with an embodiment of the present disclosure is shown. The flow process 800 may be employed with one or more of the above described transdermal optical sensing systems or variations thereof.

At step 802, a patient's or subject's testing area is cleaned. For example, the inside area of the wrist is cleaned. The cleaning may be by saline and/or alcohol solutions, or the like. It will be appreciated that the cleaning step may include additional preparation steps, such as inspecting the area on the patient, etc. Further, although referred to here with respect to the wrist, it will be appreciated that other parts of the body may be employed for purposes of the flow process 800, and the current description is not intended to be limiting to only wrist applications.

At step 804, an IRE is cleaned. The cleaning of the crystal surface may be cleaned, for example, with latex-free gauze dampened with saline solution followed by 91% rubbing alcohol. Latex-free gauze may then be used to wipe dry the surface. In some embodiments, step 804 may include disinfecting and/or sterilizing, which encompasses more than just cleaning. In some such embodiments, the transdermal optical sensing system may include an integrated cleaning system. For example, a cover of the transdermal optical sensing system may include one or more UV light sources that can be used to disinfect the IRE surface and/or other surfaces of the transdermal optical sensing system that may come into contact with a subject (e.g., patient's wrist).

Steps 802, 804 are preparation steps to ensure that measurements are no contaminated with debris, materials, oils, or the like, on human skin and/or the IRE surface.

At step 806, the transdermal optical sensing system may be operated to perform a field calibration. The field calibration step 806 may be used as a baseline to filter out background detections. For example, the field calibration step 806 may be used to create a data set to filter out ambient light, external influences, and/or impacts on the measurements taken using the transdermal optical sensing system. The field calibration may be used for detection of motion artifacts, noise correction, assessing sensor falls/drops, etc. As these things may impact the measurements taken of the subject, this information and calibration can be used to ensure proper measurements are taken or at least corrected for to remove noise or the like in the data sets. The field calibration may include noise correction, checking of accelerometer data, etc. to calibrate the system for a specific data collection.

At step 808, the subject's cleaned testing area is secured to transdermal optical sensing system such that the testing area is in contact with the cleaned IRE surface. For example, a wristband or other retention member is used to secure and/or fasten the subject's wrist to be in contact and centered with respect to the IRE. Tension of the retention member may be adjusted so that the retention member does not restrict blood flow or cause discomfort to the subject.

At step 810, the transdermal optical sensing system is operated to collect biomarker data. The biomarker data may include one or more biomarker measurements of Troponin I, Troponin T, CKMB, BNP, NTproBNP, FABP3, Myoglobins, and/or other biomarkers. In some embodiments, the data may be collected for a predetermined amount of time. For example, in one no-limiting embodiment, the transdermal optical sensing system may be operated for about 5 minutes to collect data throughout the time period. It will be appreciated that other time periods may be used, such as 1 minute, 2 minutes, 10 minutes, 15 minutes, etc. Further, in some instances, the transdermal optical sensing system may be worn for prolonged periods of time, such as hours, or even days. During such time, the transdermal optical sensing system may collect data continuously, at predetermined intervals, or upon demand (e.g., manual activation to collect biomarker data) by a doctor or other user, for example. During the biomarker data collect of step 810, time stamps may be collected and associated with the data collection, and thus time-based trending of biomarker levels may be achieved.

During step 810, the transdermal optical sensing system may be operated to generate light at one or more specific or predefined wavelengths. The generated light may be from an optical source within the transdermal optical sensing system. The light is directed into the IRE, where the light will interact with the IRE surface and the testing area of the subject. The light will be internally reflected within the IRE, and an optical detector or sensor is arranged to detect the light that interacts with the testing area. The detected light may be analyzed for peaks at one or more wavelengths to detect the presence of the biomarkers.

At step 812, the collected biomarker data is displayed. The display of the biomarker data may be on a screen or display of the transdermal optical sensing system and/or on a remote display. In some configurations, the display of the data may be on a remote personal device, such as a mobile phone, tablet, computer, or the like. In some instances, the transdermal optical sensing system may be configured to transmit the collected biomarker data directly to a connected device (e.g., by Bluetooth connection) or through a network (e.g., internet and/or cloud data system) which is then transmitted to a device for display, such as a computer or other device. In some instances, the transmission of the collected biomarker data may be through a wired connection, such as a USB connection from the transdermal optical sensing system to another device.

With the displayed biomarker data, a health professional may be able to make determinations regarding a patient's health with respect to the biomarkers detected. As such, appropriate care procedures may be implemented. Advantageously, the transdermal optical sensing systems of the present disclosure provide for real-time data collection and display and/or for data trending based on real-time, in situ measurements. In some embodiments, a blood draw may be required from the subject to confirm or further check for one or more biomarkers. It will be appreciated that the transdermal optical sensing systems of the present disclosure may be used to perform real-time, continuous monitoring of biomarkers in a non-invasive manner.

It will be appreciated that one or more of the steps of flow process 800 may be omitted or performed in a different order, without changing the scope of the process. For example, one or more of the cleaning steps 802, 804 and/or the ambient measurement of step 806 may be performed in a different order or may be omitted entirely.

The transdermal optical sensing systems of the present disclosure provide for an optical detector that is portable (e.g., palm-sized) and employs a broadband infrared light source, a germanium IRE, and a thermopile detector with filters sensitive to multiple optical ranges. In some embodiments, the thermopile detector (e.g., optical detector described above) may be configured with two different filters. In one such non-limiting embodiment, the first filter is representative of an Amide II band which is used as an internal standardizing reference and the second filter has an optical range (e.g., by frequency) chosen such that cTnI would have the largest contribution to the absorption as a function of the cTnI concentration. Due to the absence of moving parts and complex optical components, the small form factor is achieved in accordance with embodiments of the present disclosure while minimally affected by mechanical vibrations.

In accordance with some non-limiting embodiments, the filters may include a base semiconductor such as silicon, Gallium Nitride, Germanium or Indium Phosphide. Micro layers of organic or inorganic semiconductors are deposited on the base material, or it is doped with metals, to obtain a dielectric coating, the thickness of which tunes the transmission/absorption of certain wavelengths of light. The deposition methods can be Chemical Vapor Deposition, Molecular Beam Epitaxy, Metal Oxide Chemical Vapor Deposition, or energetic sputtering.

In accordance with some embodiments of the present disclosure, the effect of stray light impacting diagnostic analysis may be negated by pulsing the optical source (e.g., an optical emitter) at 4 Hz while polling the thermopile (e.g., optical detector or sensor) at 8 Hz. In accordance with embodiments of the present disclosure, the pulsing of the detector may be set at an integer multiple of the pulsing of the optical source or emitter. For example, the detector may have a pulsing rate that is double, triple, quadruple, etc. the pulsing rate of the emitter. The pulsing rate of the emitter may be selected as desired and may be a rate of 2 Hz or greater, for example. This results in recording both the on and off state of the emitter. A differential of these two states will account for the extraneous light captured by the detector. In accordance with some embodiments, based on the fourth universal definition of myocardial infarction, as informed by the $99^{th}$ percentile of troponin-I distribution in a reference population, a decision threshold of 19 ng/L is established for Myocardial Infarction diagnosis. It will be appreciated that other pulsing rates, polling rates, and decision thresholds may be employed without departing from the scope of the present disclosure.

When using Attenuated Total Reflectance (ATR) to interrogate the presence of cardiac biomarkers using infrared light, the returning evanescent light from the skin back into the IRE surface contains information that is indicative of the presence or absence of cardiac biomarkers. The penetration depth of the optical light generated by the optical sources is sufficient to interact with interstitial fluid within a patient's body. For human skin, the approximate penetration depth is about 1-10 micrometer indicating that the light could potentially interact with the epidermis and the interstitial fluid with the IRE surface placed under the wrist of a patient (palmar surface). In some embodiments, the directed light may interrogate sweat glands and/or other superficial glands through the epidermis of a patient. As such, the incident light may interrogate subsurface features of a patient and thus enable detection of specific chemicals and/or compositions that may be indicative of a patient's health.

Owing to the modality of optical data collection, in some embodiments, the IRE and/or optical detector may be susceptible to light pollution and ambient conditions. This may be mitigated by pulsing the optical source such that the detector is configured to differentially measure during both on and off states. Furthermore, in some embodiments, a blank background measurement may be conducted prior to installation on the patient. Such background measurement may be used to eliminate dependencies on ambient conditions.

In some embodiments, the optical source and the optical receiver may be configured with four optical bands to obtain a differential measurement. This enables a higher correlation to troponin by minimizing the contribution to optical absorption from other optical confounders in the measurand. Noise handling algorithms and outlier detection techniques may be implemented to improve accuracy of detection. Such techniques may be implemented by leveraging deep learning and/or neural networks, for example.

According to some embodiments of the present disclosure, a risk stratification system and method includes a non-invasive biomarker sensor, a controller, and an analyzer to detect myocardial injury or stress. In accordance with some embodiments, a wearable device includes a non-invasive biomarker sensor and a controller for sending optical signals from the non-invasive biomarker sensor to an analyzer within the device or over wireless communication to a cloud-based end point (e.g., through an internet or other wireless or wired connection). The wearable devices, in some embodiments, include an IR source, an internal reflecting element, and an IR detector with specific broad and narrow-band filters. Other optical components such as light pipes, waveguides, parabolic or flat mirrors, linear or circular polarizers may also be used to optimize the efficiency of light detection. Such additional components, for example, may be housed within the main body of the transdermal optical sensing systems described herein. The optical sources of various embodiments can include, without limitation, lasers, light emitting diodes (LEDs), radiative thermal light sources, or other such sources. The optical sources may be configured to generate and output infrared light.

For detecting one or a combination of many biomarkers representing myocardial injury or stress, optical filters that allow the passage of specific wavelengths of infrared light that are employed. The optical filters may be incorporated into the optical receivers of the transdermal optical sensing systems described above. The optical filters can be configured to allow for specific interrogation of biomarkers, or a combination thereof. For example, two absorbance wavelength ranges, 6.4-6.9 micrometers and 8-14 micrometers may be used to detect levels of biomarkers such as, but not limited to, Troponin I, Troponin T, CKMB, BNP, NTproBNP, FABP3, Myoglobins, etc. The optical filters can allow infrared light in these two absorption bands to pass through. The optical filters can be used anywhere along the light path. In one non-limiting embodiment, the filters may be directly mounted on the optical detector.

Optical detectors in accordance with embodiments of the present disclosure, and without limitation, can include thermal (pyroelectric, bolometers, microbolometers, etc.) or photonic (thermocouples, thermopiles, etc.) types. Customized optical detectors (e.g., quantum structure based) that are inherently sensitive to specific wavelength windows as mentioned above can be used in lieu of, or in combination with, the optical filters described above to perform diagnostic analysis. Further, single or multiple pass IRE may be used to allow the optical interaction of the light with that of the exposed skin that comes in contact with the IRE surface. The IRE can be made of materials including, but not limited to Germanium, Silicon, Diamond, Indium Phosphide, Sapphire, Zinc Sulphide, Zinc Selenide, Quartz, etc. The optical sensor device, which is an integration of the aforementioned components, can be mounted on or placed in contact with any part of the human body such that the IRE is directly in contact with exposed skin. In one such embodiment, the optical sensor device is fashioned as a wrist wearable where the IRE surface comes in contact with the underside of the wrist while the device is held in place by means of a strap or other retention member.

In operation of transdermal optical sensing systems described herein, the controller includes a computer-implemented method. The method is performed to characterize the differential measurement of optical intensities of light sent from the optical source and received at the optical detector, before and after it passes through the material. In some embodiments, a calibration step is performed with reference to a background data measurement (e.g., ambient conditions without a patient in contact with the IRE surface). In some embodiments, the systems and methods may include a distributed biomarker trend analysis. Such trend analysis may include, without limitation, real-time myocardium analysis based on the trend in cardiac biomarkers, in reference to baseline levels of a patient. Further, real-time myocardium analysis may be performed based on a trend in specific cardiac biomarkers, in reference to demographics 99th percentile upper reference limit. Further still, personalized triage and alert workflows for healthcare providers, patients, and caregivers may be achieved. The transdermal optical sensing systems described herein enable continuous recording and reporting of biomarker information over time. As such, biomarker baselines and trending may be achieved for individual patients. The real-time data collection and display enables improved medical diagnostics due to the ability to detect fluctuations and/or variations from a baseline or the like, for example.

According to some embodiments, the transdermal optical sensing systems can enable a risk classification of high risk, intermediate risk, and low risk of patients. Effective early risk stratification in outpatient health care facilities can help reduce the burden of chest pain evaluation in Emergency Departments and can guide high-risk patients toward more prompt care including coronary angiography and potentially earlier revascularization. For intermediate to low risk patients, continuous inpatient monitoring can also help distinguish the individuals who would benefit from an earlier invasive versus non-invasive approach, thus expediting care and discharge from the hospital. Once established as low risk, patients can proactively be monitored for recurring cardiac complications.

Advantageously, embodiments described herein provide for non-invasive devices for monitoring patient wellbeing. In accordance with some embodiments, a patient-centric modality for troponin-I monitoring is provided that can inform efficient triaging and timely intervention in a cardiac clinical workflow. The devices and processes disclosed herein enable remote monitoring capability to empower cardiologists in determining a timely clinical course of action to prevent unnecessary myocardial injury.

Also disclosed and described are wearable sensors that may be worn in a watch-style configuration and may be used in combination with a worn heart rate monitor, such as an EKG vest, or other medical monitoring system. That is, embodiments of the present disclosure may be employed in combination with other health sensors to develop and monitor the health of a patient. It will be appreciated that such heart rate monitors or other monitoring devices and systems may be employed with any of the transdermal optical sensing systems described herein, and such combination of devices is not limited to the watch-type systems. Such use of multiple devices for multiple different patient variables (e.g., biomarker levels, heart rate, blood pressure, etc.) may enable further improved patient health care outcomes and responses.

Aspects of technical solutions described herein further facilitate using transdermal infrared optics to discover infraspectral markers ("inframarker"). The infraspectral markers are associated with one or more diseases in some examples. For example, the presence of one or more infraspectral markers in a transdermal optical scan, performed according to one or more aspects described herein, can be mapped to a disease or physiological state such as, cancer, diabetes, a chronic condition, a comorbidity, a rare disease, an allergy or any other condition. An "inframarker" as used herein is an optical infrared signature representative of a biomarker e.g., troponin-I. An inframarker can be any form of infrared signature such as an absorption, a transmission, a reflection, or a combination thereof. For example, a unique combination of absorption peaks from an infraspectral scan can be inframarkers for biomarkers such as, h-FABP (fatty acid binding protein) or CEA (carcinoembryonic antigen). It is understood that other types of inframarkers and biomarkers can be used in other aspects of the technical solutions described herein. Further, "an infraprofile" refers to an optical infrared signature representative of a physiological condition e.g., Myocardial Infarction. An infraprofile can include one or more inframarkers. For example, a physiological condition can be represented by one or more biomarkers, and accordingly, the infraprofile for that physiological condition includes the corresponding one or more inframarkers. It will be appreciated that an inframarker may not necessarily have to represent a known biomarker. Some aspects of the technical solutions described herein can identify a unique inframarker profile that represents a physiological state of the subject 905 without corresponding to any known biomarker. In other words, the infraprofile facilitates identifying a physiological state of the subject 905 directly (without having to determine a corresponding biomarker).

Figure 9:
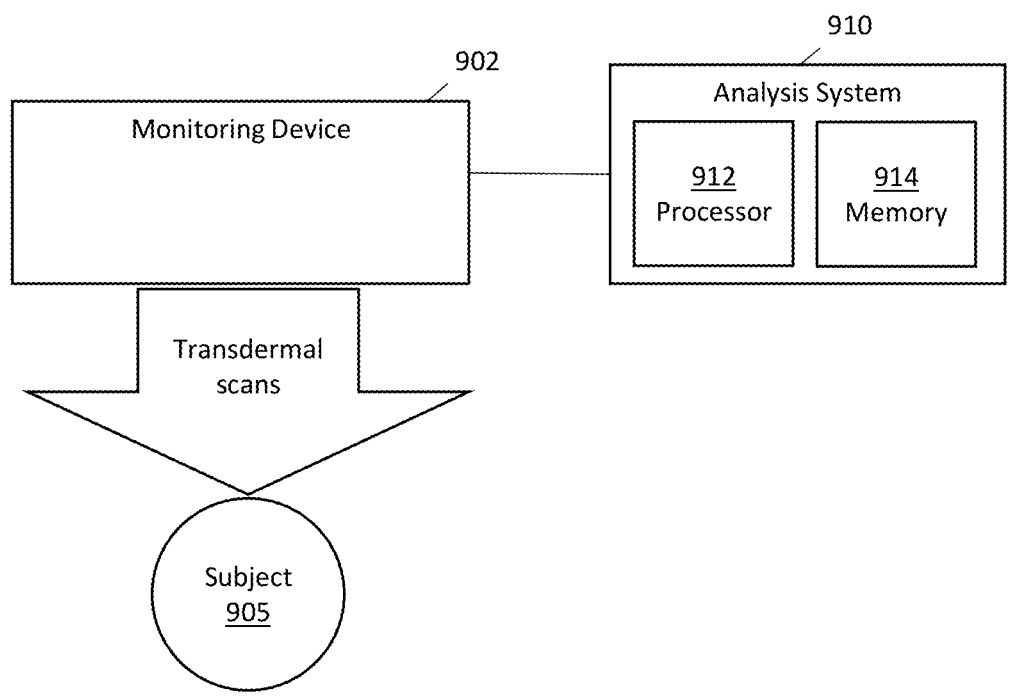
FIG. 9 depicts a block diagram for a system that includes a monitoring device for capturing a transdermal optical scan of a subject according to one or more aspects of the present technical solutions.

FIG. 9 depicts a block diagram for a system that includes a monitoring device for capturing a transdermal optical scan of a subject according to one or more aspects of the present technical solutions. The system 900 includes, among other components that are not shown, a subject 905 (or user), a monitoring device 902, and an analysis system 910. The subject 905 is a human user who is being analyzed to predict if the subject 905 has a particular physiological condition, or at least infraspectral marker.

The monitoring device 902 can be any of the transdermal optical sensing devices described herein. In one or more examples, the data from the monitoring device 902 is transmitted in the form of electronic signals to an analysis system 910. In one or more examples, the data is transmitted as streaming data. The electronic signals transmitted can be analog signals in one or more examples. Alternatively, or in addition, the electronic signals can include digital signals. Further, in one or more examples, the streaming data includes separate electronic signals from each of the multiple sensors that can be part of the monitoring device 902. For example, the streaming data can include 6, 7, or any other number of ECG sensor signals and one or more biomarker sensor signals. Other combinations of sensor signals are also possible in other aspects of the present technical solutions.

In one or more examples, the analysis system 910, based on the sensor signals, can determine an automated mapping between a phenotype for the patho-physiological condition (e.g., biomarker trends, phases of a disease, etc.) and one or more inframarkers to identify an optimal inframarker configuration for detecting the condition. An "inframarker configuration" includes one or more settings of the monitoring device 902 to capture measurements (e.g., absorption, reflection, etc.) for an inframarker using total internal reflection. In some aspects, the measurements captured for an inframarker can be a set of one or more units of wavelength in the optical scan/measurements (i.e., infraspectral scan). The inframarker configuration can further include a value of a "delta" associated with an inframarker, wherein the delta is a dynamic range used to determine if there is a spike/dip in the inframarker measurement, which corresponds to a spike/dip in the amount of the corresponding biomarker in the subject 905. In one or more aspects, the analysis system 910 performs the identification of the inframarker configuration, including determining the delta, using static algorithms or dynamic algorithms. In some aspects, the dynamic algorithms include machine learning algorithms (e.g., neural network). In some aspects, the inframarker configuration is adjusted by clinicians via a visualization tool provided by the analysis system 910.

In one or more aspects, the inframarker configuration can be identified for a certain inframarker associated with a physiological state when certain conditions are determined to be satisfied using machine learning techniques. For example, the inframarker configuration is generated when the transdermal infrared spectral scans includes a vector A (input measurements) that is mapped to known concentrations of a blood based protein as vector B (output). The inframarker configuration includes a vector in latent space that represents the ideal combination of optical measurements (e.g., infraspectral peaks, absorption values, etc.) that generates vector B from vector A. The inframarker configuration could also be generated via static or other dynamic techniques where various combinations of measurements from the transdermal optical scans are correlated with blood concentration levels using techniques such as regression analysis.

In one or more aspects, the delta value facilitates detecting a condition associated with one or more inframarkers indicative of a condition (phenotype). For example, the condition can be a relatively elevated level of an inframarker. For example, an elevated level of the inframarker associated with the biomarker troponin is indicative of acute myocardial infarction; or an elevated level of an inframarker representing BNP is indicative of acute heart failure. It is understood that the above conditions are exemplary, and that other conditions can also be used to identify inframarkers and/or corresponding phenotypes. As noted earlier, an infraprofile provides a unique combination of inframarkers, (e.g., a combination of infraspectral measurements) representing multiple biomarkers such as CRP, h-FABP, CTNI, CK-MB, or other unknown inflammatory biomarkers). An infraprofile can be identified using the system 900 for a particular condition or a combination of conditions.

Further, a time series analysis of an infraspectral scan can identify an underlying phase of a disease (another phenotype). For example, a unique combination of optical measurements (e.g., relative peak, dip, etc.) in the transdermal infraspectral scan can identify coronary artery disease in its stable chronic state vs a reversible state of ischemia (acute myocardial injury) vs an irreversible state of ischemia (myocardial infarction) vs an ischemia in a state of reinfarction. In another example, the inframarker(s) facilitate identifying as the abnormal cells of a tumor spread to tissue and involve various levels of lymph nodes before metastasizing i.e., stage 1 cancer vs stage 2 cancer vs stage 3 cancer vs stage 4 cancer. Such identification, of different stages of a disease, can be achieved by using the aspects of the technical solutions described herein based on different infra markers released by the subject 905 in the different stages. For example, myocardial ischemia can release h-FABP, CRP, suPAR while infarction releases CTNI in addition to hFABP, CRP and suPAR. Stage 3 cancer (localized) releases certain signals and biomarkers while stage 4 (regional spread) and stage 5 (metastasized) release other signals and biomarkers. Based on the detection of these biomarkers (i.e., patho-physiological conditions) transdermally and in a continuous manner, technical solutions described herein facilitate improved triage and treatment of the conditions, along with remote patient monitoring for these conditions.

An inframarker configuration can include one or more settings of the monitoring device 902 to be used to predict presence (or absence) of the physiological condition such as a biomarker in the subject 905 using a transdermal optical scan. Typically, in existing techniques, detecting a biomarker is performed using invasive tests such as, drawing blood or other types of fluids or matter from the subject. Further, detecting the biomarker is performed offline, in a clean laboratory environment, and can require a delay until the report comes back. This delay can potentially delay the subject 905 from receiving treatment, and in some cases, the "correct" treatment based on the information conveyed by the presence/absence of the biomarker.

Aspects of the present technical solutions address such challenges by facilitating a prediction of the presence/absence of the biomarker faster and in a non-invasive manner by performing a transdermal optical scan of the subject 905 using the monitoring device 902. The monitoring device 902 is configured based on the physiological condition(s) to be detected. In some aspects, the monitoring device 902 is automatically reconfigured through a list of configurations respectively used to predict a list of physiological conditions. The list of physiological conditions can be input and, in one or more examples, the configurations of the monitoring device 902 can be automatically changed, or adjusted by clinicians via a visualization tool.

It should be noted that although the analysis system 910 is shown separate from the monitoring device 902, in one or more examples, the analysis system 910 can be part of the monitoring device 902 itself (or vice versa).

The analysis system 910 can be a computing device, such as a server computer, a desktop computer, a laptop computer, a tablet computer, a phone, or any other such electronic device. The analysis system 910 includes a processing unit 912 and a memory 914. The processing unit 912 includes one or more processors that execute computer executable instructions. The memory 914 includes volatile/non-volatile memory device that facilitates the execution of the computer executable instructions. In one or more examples, the memory 914 stores the computer executable instructions. Further, the memory 914 can include media, text, databases, data structures, files, and other such electronic data to facilitate the execution of the computer executable instructions.

The one or more settings in the inframarker configuration to predict the physiological condition can include one or more wavelength units (e.g., 2000 to 800 cm-1 (5 µm to 12.5 µm) range) of light to be emitted by the monitoring device 902. The inframarker configuration can further include one or more thresholds respectively for the one or more wavelengths being used to scan the subject 905. A threshold is used to predict whether the subject 905 may have the physiological condition by comparing a corresponding measurement from the monitoring device 902 with that threshold. In some examples, the prediction may be based on a combination of measurements.

In one or more examples, the monitoring device 902 uses spectroscopy such as in near, mid, and far-infrared range, microwave range, visible region, or other such range of the electromagnetic spectrum. The range can be varied based on the biomarker (i.e., protein/chemical) being predicted. The monitoring device 902 uses infrared (IR) spectroscopy that provides an optical fingerprint of the biomarker when scanned in the 2000 to 800 cm-1 (5 µm to 12.5 µm) range. This detection can be used to identify, differentiate and quantify the amount of the biomarkers (for example, troponin I, h-FABP, etc.) in whole blood using one or more inframarkers. An inframarker is a fingerprint for a biomarker, and can be a unique combination of absorbance peaks (or any other measurements) within a spectral range in which the concentration of the biomarker in a biofluid can be detected using total internal reflection of the monitoring device 902. Absorbance peaks are monitored based on amplitude of the reflected light that is absorbed by a photodetector in the monitoring device 902 in one or more examples.

In one or more aspects, once one or more transdermal optical scans of the subject 905 are performed, the analysis system 910 can generate the infraprofile of the subject 905. The infraprofile can predict presence/absence of one or more inframarkers (i.e., biomarkers), and in turn, physiological conditions of the subject 905. Based on the infraprofile, a medical personnel (e.g., doctor, nurse, etc.) can recommend a treatment, test, etc., for the subject. For example, based on the prediction from the transdermal optical scan, the medical personnel may determine whether an invasive test is required. Alternatively, or in addition, based on the prediction, the medical personnel can determine a certain course of treatment for the subject 905.

In some cases, the transdermal optical scan can be performed in a continuous manner by the monitoring device 902, for example, a transdermal optical scan is performed at predetermined intervals. Based on the measurements from the continuous monitoring, trends of the biomarkers can be non-invasively determined by the analysis system 910 at predetermined intervals. Accordingly, real time analysis and prediction of the biomarker (i.e., physiological condition) of the subject 905 can be performed in a continuous manner. Here "continuous manner" includes performing at least two transdermal optical scans every minute in some aspects. In other words, within a certain predetermined duration, at least two transdermal optical scans are performed, where the predetermined duration can be one of 45 seconds, 60 seconds, 90 seconds, 120 seconds, 150 seconds, 180 seconds, 300 seconds, or any other such predetermined duration. In yet other words, two successive transdermal optical scans are performed within a predetermined interval of each other such as 45 seconds, 60 seconds, 90 seconds, 120 seconds, 150 seconds, 180 seconds, 300 seconds, or any other such predetermined interval. It is understood that other intervals can be selected.

Aspects of the present technical solutions further facilitate personalized triage and alert workflow baseline and trending information. For example, a baseline of the measurements from the monitoring device 902 for a particular subject 905 can be established by capturing the transdermal optical scans of the subject 905 for at least a predetermined times/duration. For example, once at least 15 transdermal optical scans are performed for the subject 905, those 15 scans are used to establish baseline measurements for a particular biomarker (e.g., troponin I, FABP3, etc.) for the subject 905. Subsequently, further transdermal optical scans (e.g., the 16th scan) of the subject 905 are compared to the established baseline to determine whether a change (delta) in one or more measurements exceeds (spike/dip) a predetermined threshold. In such cases, further actions can be taken for the subject 905. In other examples, instead of a personalized baseline, a predetermined baseline can be used to compare the trends of the measurements of the subject 905. A separate baseline (personalized or predetermined) is used for each measurement captured in the non-invasive transdermal optical scan. In some cases, a personalized baseline (for a particular subject) is used for a first inframarker (e.g., h-FABP) and a predetermined baseline (non-personalized/common across multiple subjects) is used for a second inframarker (e.g., troponin I).

Figure 10:
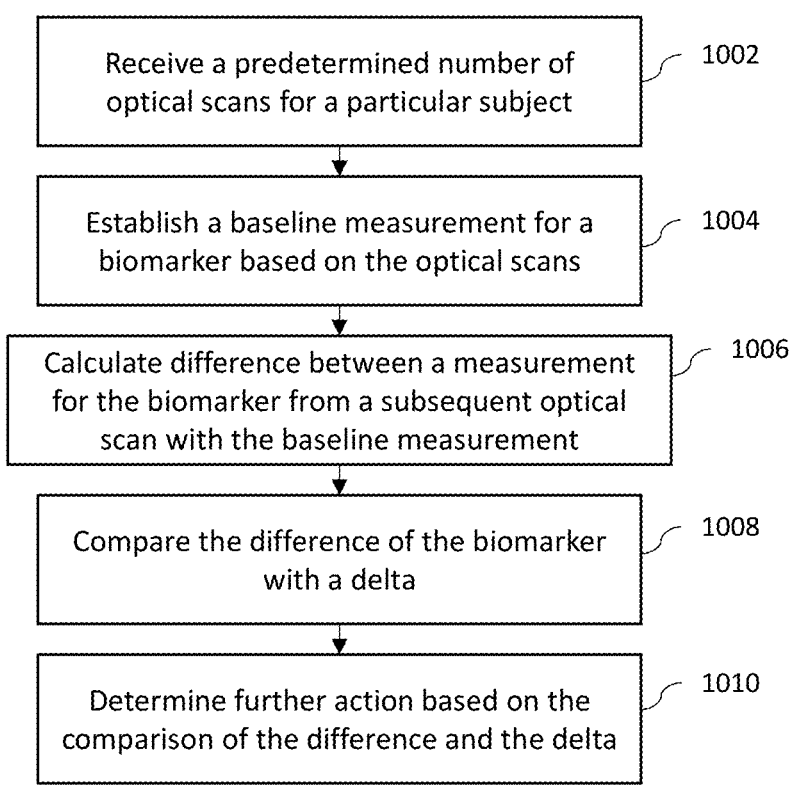
FIG. 10 depicts a flowchart of a method for continuous monitoring a subject for one or more biomarkers using the optical sensing system according to one or more aspects.

FIG. 10 depicts a flowchart of a method for continuous monitoring a subject for one or more biomarkers using the optical sensing system according to one or more aspects. The method 1000 includes, at block 1002, receiving, by the analysis system 910, data from at least a predetermined number of optical scans performed on a particular subject 905. The predetermined number can be 5, 10, 15, or any other number that the analysis system 910 can use to establish a personalized baseline measurement for the subject 905.

At block 1004, the analysis system 910 establishes the baseline measurement for at least one inframarker, i.e., biomarker (e.g., troponin I) using the optical scans. The baseline measurement is established using a statistical technique such as calculating the mean, geometric mean, weighted mean, trendline computation, logistic regression, or any other linear or non-linear statistical computation. In some aspects, the baseline is established using machine learning, for example, using algorithms such as multi-parameter deep neural network.

In some aspects, when using machine learning to establish the baseline, the analysis system 910 automatically adjusts the monitoring device 902. The configurability of the monitoring device 902 can facilitate adjusting one or more settings such as delta value, wavelength of the light emitted and/or detected, intensity of light, electric voltage, electric current, pulse rate of the light emitter, pulse rate of the light receiver, etc. Here, the delta value is used to compare deviations of the measurements from the personalized baseline(s), and in response to the deviation being larger than the delta value, triggering one or more actions as described herein.

The analysis system 910 can conduct a predetermined number of optical scans of the subject 905 using a particular configuration, i.e., settings of the monitoring device 902. The captured optical scans are analyzed to establish the baseline measurements. If a satisfactory baseline measurement (e.g., comparing with ground truth data) cannot be established for a physiological identifier of the subject 905 using the machine learning algorithm, the configuration of the monitoring device 902 is adjusted by the analysis system 910, and the baseline establishment is repeated using the machine learning. Such a process is repeated until a satisfactory baseline is established for a physiological marker of the subject 905. In some examples, a baseline measurement is established for multiple physiological markers for the subject in this manner.

At block 1006, data from subsequent optical scans by the monitoring device 902 is compared by the analysis system 910 with the established baseline to calculate a difference between a measurement corresponding to the physiological identifier (e.g., biomarker) being observed with the baseline measurement. It should be noted that in some aspects, the difference can be based on measurements of multiple parameters. For example, the physiological identifier can be based on measurements of two or more units of wavelengths. Accordingly, the delta can be based on (e.g., mean, sum, median, etc.) of the differences between measurements of the two or more parameters in a transdermal optical scan and corresponding baseline measurements.

At block 1008, the calculated difference is compared with a predetermined threshold, i.e., the delta value. If the difference exceeds the delta, a spike or a dip can be identified. In some aspects, an absolute value (modulus) of the difference is used to compare with the delta.

At block 1010, a further action is determined based on the comparison of the difference and the delta. For example, if a spike/dip is not identified, i.e., the difference does not exceed the delta value, the continuous monitoring is continued. Alternatively, if a spike/dip is detected, additional tests may be performed on the subject 905. In yet other aspects, in case of the spike/dip being detected, the configuration of the monitoring device 902 is adjusted to perform additional optical scans on the subject 905. In some examples, if the difference exceeds the delta only by a minimal amount (e.g., a second predetermined value), the configuration of the monitoring device 902 is adjusted automatically to detect fluctuations and/or variations from the baseline. In some aspects, if the delta is exceeded, a notification to the medical personnel can be triggered.

The analysis system 910 can access the configurability of the monitoring device 902 and adjust one or more settings of the monitoring device 902 and request additional optical scans using the adjusted settings. For example, the adjustments can include changing the wavelengths of light emitted and/or detected, intensity of light, internal angles of reflection, electric voltage applied, electric current, or any other setting that can cause a particular measurement to be captured in a more accurate manner. Such automatic configurability (i.e., adjustment of configuration) of the monitoring device can improve accuracy of the detecting a physiological identifier/marker for the subject 905 in the optical scan (i.e., non-invasive, transdermal manner). In some cases, a user, such as a nurse, clinician, doctor, or any other personnel, can review and/or update the adjustments being made to the monitoring device 902. For example, the user can view the adjustments to the settings of the monitoring device 902 via a user-interface, for example, a display of the analysis system 910. The user can make additional changes to the adjusted settings, which are subsequently sent by the analysis system 910 to the monitoring device 902.

Alternatively, or in addition, frequency of capturing the transdermal optical scans can also be changed in response to the delta being within a predetermined range. For example, frequency of capturing and analyzing the transdermal optical scans is lower (e.g., scan every 15 minutes) when the delta is in a first predetermined ("safe") range, whereas when the delta is in a second predetermined ("critical") range, the frequency of capturing and analyzing the transdermal optical scans is adjusted higher (e.g., scan every five minutes). It is understood that additional predetermined ranges and corresponding monitoring frequencies can be used in other aspects of the technical solutions herein. In some aspects, in addition to updating the frequency, alert notifications/reports for subject 905 are sent to medical personnel and/or caregivers.

In some aspects, the analysis system 910 already knows that the subject 905 has a certain physiological state, e.g., a disease. The analysis system 910, in conjunction with the monitoring device 902, can be used to determine an inframarker configuration (i.e., settings of the monitoring device 902) that can detect an inframarker in the optical scans for the subject, i.e., a measurement in the subject 905 that corresponds to the physiological state.

Figure 11:
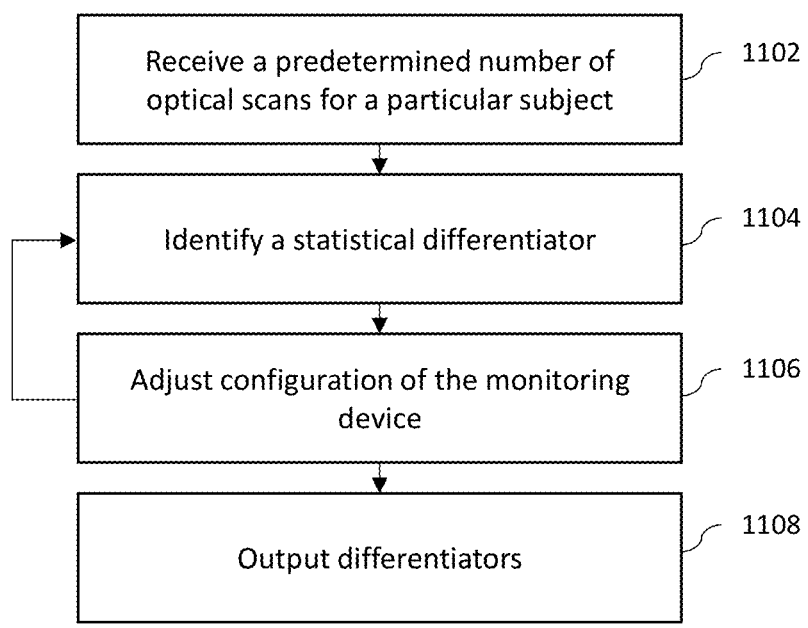
FIG. 11 depicts a flowchart of a method for establishing an inframarker configuration for a physiological state according to one or more aspects.

FIG. 11 depicts a flowchart of a method for establishing an inframarker configuration for a physiological state according to one or more aspects. The analysis system 910 causes the monitoring device 902 to capture at least a predetermined number of optical scans of the subject 905 using a first configuration (i.e., settings) of the monitoring device 902, at block 1102. At block 1104, the measurements from the optical scans are analyzed to identify one or more differentiators, e.g., spikes, dips, trends, or any other statistically relevant markers. The differentiators are identified using machine learning, in one or more examples. In some examples, temporal analysis of time series data using recurrent neural network (RNN) is performed to identify the one or more differentiators. In some examples, the RNN identifies various differentiators that can serve as predetermined thresholds (delta values) for appropriate trigger actions (higher frequency monitoring and analysis/alerts/notifications/reporting.

At block 1106, the analysis system 910 adjusts one or more settings of the monitoring device 902 to generate a second configuration. In one or more aspects, the second configuration is generated in response to differentiators not being identified using the first configuration. In some aspects, the analysis system 910 continues to generate additional inframarker configurations until one or more differentiators are identified. Alternatively, or in addition, the analysis system 910 generates at least a predetermined number of inframarker configurations. One or more differentiators are sought (1104) after each change in configuration.

At block 1108, after a predetermined number of configurations, after a predetermined duration, or in response to a manual intervention, the analysis system 910 exits the loop (1104, 1106), and outputs the identified differentiators.

In some aspects, the configuration of the monitoring device 902 for identifying a physiological state is used automatically when a subject 905 with that physiological state is being monitored by the monitoring device 902.

Aspects of the present technical solutions further facilitate remote patient monitoring. For example, the monitoring device 902 can be used by the subject 905 when s/he is away from a medical institution (e.g., hospital, research institute, etc.). The measurements from the monitoring device 902 can be transmitted to the analysis system 910, which may or may not be remote from the monitoring device 902. The infraprofile that is generated may be transmitted to a medical personnel, who may be remote from the subject (and hence, monitoring device 902) and suggest the further course of action for the subject 905.

According to one or more aspects, a system includes a transdermal optical monitoring device, and an analysis system in communication with the transdermal optical monitoring device. The analysis system performs a method that includes receiving, from the transdermal optical monitoring device, a predetermined number of optical scans, each optical scan comprising data indicative of absorption of light by a subject, the absorption caused in response to the transdermal optical monitoring device transmitting light pulses towards the subject in a transdermal manner. The method further includes establishing a baseline measurement for an inframarker based on the data from the predetermined number of optical scans, the inframarker is indicative of a biomarker of a physiological state of the subject, the inframarker is based on one or more measurements from an optical scan. The method further includes receiving, from the optical monitoring device, a first optical scan comprising a first measurement of the inframarker. The method further includes calculating a difference between the first measurement of the inframarker and the baseline measurement of the inframarker. The method further includes, in response to the difference exceeding a predetermined delta, notifying that the subject has the physiological state.

In one or more aspects, the analysis system automatically adjusts one or more settings of the transdermal optical monitoring device.

In one or more aspects, the analysis system adjusts the one or more settings of the transdermal optical monitoring device to establish the baseline measurement of the inframarker.

In one or more aspects, the analysis system adjusts the one or more settings of the transdermal optical monitoring device in response to the difference being less than a second predetermined threshold.

In one or more aspects, the analysis system causes the optical monitoring device to capture at least two optical scans within a predetermined duration.

In one or more aspects, the predetermined duration is less than one minute.

In one or more aspects, the transdermal optical monitoring device is configured to detect light at a range of 6.4-6.9 micrometers and a range of 8-14 micrometers in an optical scan.

In one or more aspects, the transdermal optical monitoring device is configured to generate light at a predetermined pulse rate and the transdermal optical monitoring device is configured to detect at a predetermined polling rate.

According to one or more aspects, a computer-implemented method includes receiving, by one or more processors, from an optical monitoring device, an optical scan, wherein the optical scan comprises a first measurement of an inframarker, the inframarker is indicative of one or more optical measurements representative of a physiological identifier of a physiological state of a subject. The method further includes calculating, by the one or more processors, a difference between the first measurement of the inframarker and a baseline measurement of the inframarker, the baseline measurement being customized for the subject. The method further includes, in response to the difference exceeding a delta, notifying, by the one or more processors, that the subject has the physiological state.

In one or more aspects, the physiological identifier comprises a biomarker for the physiological state.

In one or more aspects, the method further includes receiving, by the one or more processors, from the optical monitoring device, a predetermined number of optical scans. The method further includes customizing the baseline measurement of the inframarker for the subject based on the data from the predetermined number of optical scans.

In one or more aspects, the analysis system adjusts the one or more settings of the optical monitoring device to establish the baseline measurement of the inframarker.

In one or more aspects, the analysis system adjusts the one or more settings of the optical monitoring device in response to the difference being in a predetermined range.

In one or more aspects, the analysis system continuously monitors the subject by causing the optical monitoring device to capture at least two optical scans within a predetermined duration.

In one or more aspects, the optical monitoring device is configured to detect light at a range of 6.4-6.9 micrometers and a range of 8-14 micrometers in an optical scan.

According to one or more aspects, an analysis system includes a memory, and one or more processors coupled with the memory. The one or more processors access a plurality of optical scans of a subject, the subject known to have a physiological state, the optical scans captured by an optical monitoring device in a transdermal manner. Further, the one or more processors identify an infraprofile by analyzing the optical scans, the infraprofile is indicative of the physiological state of the subject the infraprofile comprises one or more inframarkers based on optical measurements from the optical scans. Further, the one or more processors output the infraprofile as a non-invasive identifier of the physiological state of the subject.

In one or more aspects, the one or more processors are further configured to access a first optical scan of the subject, the first optical scan comprising a first measurement of an inframarker. The one or more processors further calculate a difference between the first measurement of the inframarker and a baseline measurement of the inframarker. The one or more processors, in response to the difference exceeding a delta, add the inframarker to the infraprofile of the physiological state.

In one or more aspects, the baseline measurement is customized for the subject.

In one or more aspects, the baseline measurement of the inframarker is customized for the subject based on the data from the predetermined number of optical scans.

In one or more aspects, the one or more processors are further configured to cause the optical monitoring device to collect optical scans continuously over a predetermined amount of time.

The terminology used herein is for the purpose of describing particular embodiments only and is not intended to be limiting of the present disclosure. The terms "about" and/or "substantially" are intended to include the degree of error associated with measurement of the particular quantity based upon the equipment available at the time of filing the application. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A system comprising:
    a transdermal optical monitoring device configured to perform Attenuated Total Reflectance to generate an evanescent wave to interrogate an epidermis of a subject;
    an analysis system in communication with the transdermal optical monitoring device, the analysis system configured to perform a method comprising:
    receiving, from the transdermal optical monitoring device, a predetermined number of optical scans, each of the optical scans comprising data indicative of absorption of light at a range of 6.4-6.9 micrometers and a range of 8-14 micrometers by the subject, the absorption caused in response to the transdermal optical monitoring device transmitting light pulses towards the subject in a transdermal manner;
    establishing a baseline measurement for an inframarker based on the data from the predetermined number of optical scans, the inframarker being indicative of a single one or a combination of biomarkers representing a physiological state of the subject, including myocardial injury and/or myocardial stress;
    receiving, from the transdermal optical monitoring device, a first optical scan comprising a first measurement of the inframarker, the first optical scan being different from the predetermined number of optical scans;
    calculating a difference between the first measurement of the inframarker and the baseline measurement of the inframarker;
    in response to the difference exceeding a predetermined delta, detecting a change in the physiological state of the subject; and
    adjusting a frequency of capturing the data from the transdermal optical monitoring device based on a magnitude of the predetermined delta, the frequency being lower when the predetermined delta is within a first predefined range, the frequency being higher when the predetermined delta is within a second predefined range.

2. The system of claim 1, wherein the analysis system automatically adjusts one or more settings of the transdermal optical monitoring device.

3. The system of claim 2, wherein the analysis system adjusts the one or more settings of the transdermal optical monitoring device to establish the baseline measurement of the inframarker.

4. The system of claim 2, wherein the analysis system adjusts the one or more settings of the transdermal optical monitoring device in response to the difference being less than a predetermined reference limit.

5. The system of claim 1, wherein the analysis system causes the transdermal optical monitoring device to capture at least two optical scans in the predetermined number of optical scans within a predetermined duration.

6. The system of claim 5, wherein the predetermined duration is less than one minute.

7. The system of claim 1, wherein the transdermal optical monitoring device is configured to detect light in each of the predetermined number of optical scans.

8. The system of claim 1, wherein the transdermal optical monitoring device is configured to generate light at a predetermined pulse rate and the transdermal optical monitoring device is configured to detect at a predetermined polling rate.

9. The system of claim 1, wherein the first predefined range is categorized as safe, and the second predefined range is categorized as critical.

10. The system of claim 1, wherein the transdermal optical monitoring device includes an optical source and an optical detector, and a polling rate of the optical detector is selected to be an integer multiple of a pulsing rate of the optical source.

11. A computer-implemented method, comprising:
    receiving, by one or more processors in an analysis system, from an optical monitoring device, a first optical scan, wherein the first optical scan comprises a first measurement of an inframarker, the optical monitoring device being configured to perform Attenuated Total Reflectance to generate an evanescent wave to interrogate an epidermis of a subject, the inframarker being indicative of one or more optical measurements representative of a physiological identifier of a physiological state of the subject, the physiological state including myocardial injury and/or myocardial stress;
    calculating, by the one or more processors, a difference between the first measurement of the inframarker and a baseline measurement of the inframarker, the baseline measurement being customized for the subject, the optical monitoring device being configured to detect light at a range of 6.4-6.9 micrometers and a range of 8-14 micrometers in the first optical scan;
    in response to the difference exceeding a predetermined delta, detecting a change, by the one or more processors, in the physiological state of the subject; and
    adjusting a frequency of capturing data from the optical monitoring device based on a magnitude of the predetermined delta, the frequency being lower when the predetermined delta is within a first predefined range, the frequency being higher when the predetermined delta is within a second predefined range.

12. The computer-implemented method of claim 11, wherein the physiological identifier comprises a single one or a combination of biomarkers for the physiological state.

13. The computer-implemented method of claim 11, further comprising:

receiving, by the one or more processors, from the optical monitoring device, a predetermined number of optical scans different from the first optical scan; and customizing the baseline measurement of the inframarker for the subject based on the data from the predetermined number of optical scans.

14. The computer-implemented method of claim 13, wherein the analysis system adjusts one or more settings of the optical monitoring device to establish the baseline measurement of the inframarker.

15. The computer-implemented method of claim 13, wherein the analysis system continuously monitors the subject by causing the optical monitoring device to capture at least two optical scans in the predetermined number of optical scans within a predetermined duration.

16. The computer-implemented method of claim 13, wherein the optical monitoring device is configured to detect light at the range of 6.4-6.9 micrometers and the range of 8-14 micrometers in each of the predetermined number of optical scans; and the optical monitoring device includes an optical source and an optical detector, a polling rate of the optical detector being selected to be an integer multiple of a pulsing rate of the optical source.

17. The computer-implemented method of claim 11, wherein the first predefined range is categorized as safe, and the second predefined range is categorized as critical.

* * * * *